(12) United States Patent
Gadue et al.

(10) Patent No.: US 9,476,030 B2
(45) Date of Patent: Oct. 25, 2016

(54) SELF-RENEWING ENDODERMAL PROGENITOR LINES GENERATED FROM HUMAN PLURIPOTENT STEM CELLS AND METHODS OF USE THEREOF

(71) Applicant: The Children's Hospital of Philadelphia, Philadelphia, PA (US)

(72) Inventors: Paul Gadue, Philadelphia, PA (US); Deborah French, Newark, DE (US); Xin Cheng, Briarwood, NY (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 57 days.

(21) Appl. No.: 14/138,963

(22) Filed: Dec. 23, 2013

(65) Prior Publication Data

US 2014/0141509 A1 May 22, 2014

Related U.S. Application Data

(63) Continuation-in-part of application No. PCT/US2012/044096, filed on Jun. 25, 2012.

(60) Provisional application No. 61/500,442, filed on Jun. 23, 2011.

(51) Int. Cl.
*C12N 5/071* (2010.01)

(52) U.S. Cl.
CPC ............. *C12N 5/0678* (2013.01); *C12N 5/068* (2013.01); *C12N 5/0672* (2013.01); *C12N 2501/115* (2013.01); *C12N 2501/155* (2013.01); *C12N 2501/16* (2013.01); *C12N 2501/165* (2013.01); *C12N 2502/13* (2013.01); *C12N 2506/02* (2013.01); *C12N 2506/45* (2013.01); *C12N 2533/90* (2013.01)

(58) Field of Classification Search
CPC ........................... C12N 5/0678; C12N 5/0672
See application file for complete search history.

(56) References Cited

U.S. PATENT DOCUMENTS

| | | |
|---|---|---|
| 6,479,283 B1 | 11/2002 | Mansson et al. |
| 2009/0092586 A1 | 4/2009 | Verfaillie et al. |
| 2009/0181453 A1* | 7/2009 | Keller .................. C12N 5/0606 435/325 |
| 2009/0280096 A1 | 11/2009 | Kubo et al. |
| 2010/0190202 A1 | 7/2010 | Heins et al. |
| 2010/0255580 A1 | 10/2010 | Rezania |
| 2010/0261277 A1 | 10/2010 | Colton et al. |
| 2010/0279275 A1 | 11/2010 | Panja |
| 2011/0014692 A1 | 1/2011 | Lim et al. |
| 2011/0135610 A1 | 6/2011 | Reid et al. |

OTHER PUBLICATIONS

Séguin et al. (Cell Stem Cell. 2008; 3: 182-195).*
Séguin et al. (Cell Stem Cell. 2008; 3: Supplemental Data).*

* cited by examiner

*Primary Examiner* — Scott Long
(74) *Attorney, Agent, or Firm* — Kathleen D. Rigaut; Dann, Dorfman, Herrell & Skillman

(57) ABSTRACT

Self-renewing endodermal progenitor lines generated from human pluripotent stem cells and methods of use thereof are disclosed.

7 Claims, 15 Drawing Sheets

SELF-RENEWING ENDODERMAL PROGENITOR LINES GENERATED FROM HUMAN PLURIPOTENT STEM CELLS AND METHODS OF USE THEREOF

This application is a continuation in part of PCT/US2012/44096 filed Jun. 25, 2012, which in turn claims priority to U.S. Provisional Application No. 61/500,442 filed Jun. 23, 2011. The entire contents being incorporated herein by reference as though set forth in full.

FIELD OF THE INVENTION

This invention relates to the fields of cell based and transplantation therapies. More specifically, the invention provides methods and compositions for optimized growth conditions for the generation of endodermal progenitor cells obtained from human embryonic and induced pluripotent stem cells.

BACKGROUND OF THE INVENTION

Several publications and patent documents are cited throughout the specification in order to describe the state of the art to which this invention pertains. Each of these citations is incorporated herein by reference as though set forth in full.

Human pluripotent stem cells (PSCs), including embryonic stem cells (ESCs) and induced pluripotent stem cells (iPSCs), hold tremendous promise for both basic biology and cell based therapies due to their unlimited in vitro proliferation capacity and their potential to generate all tissue types (Murry and Keller 2008; Stadtfeld and Hochedlinger et al., 2010). Upon in vitro differentiation, these stem cell populations recapitulate early embryonic development, giving rise to a spectrum of mature cell types (Murry and Keller 2008).

During embryogenesis, the blastocyst inner cell mass gives rise to an epithelial population known as the epiblast. These cells traverse the primitive streak during gastrulation, giving rise to mesoderm and definitive endoderm (DE) (Lu et al., 2001). The epithelial sheet of nascent DE then folds to form the primitive gut tube consisting of three major domains along the anterior-posterior axis: the foregut, midgut and hindgut. These domains are further refined into specific regions from which the rudiments of various endodermal organs bud (Zorn and Wells, 2009). The foregut eventually gives rise to esophagus, trachea, lungs, thyroid, parathyroid, thymus, stomach, liver, biliary system and pancreas, while the midgut and hindgut form the small intestine and colon.

Endoderm-derived tissues, including liver and pancreas, are potentially useful for cell replacement therapies. It is possible to generate DE and its derivative lineages from PSCs in vitro through sequential exposure to cytokines that mimic embryonic morphogenesis. In this fashion, hepatic, intestinal and pancreatic cells can be produced from ESCs and iPSCs (D'Amour et al., 2006; Gouon-Evans et al., 2006; Basma et al., 2009; Spence et al., 2011). While these studies highlight the promise of PSC-derived endodermal tissues for transplantation therapies, several obstacles remain. Endodermal cells generated from PSCs tend to display immature phenotypes and in many instances are not fully functional. For example, most pancreatic β-cells currently generated in vitro from human ESCs are poly-hormonal and not glucose responsive (D'Amour et al., 2006; Nostro et al., 2011). In addition, the pluripotent nature of ESCs and iPSCs results in production of multiple cells types from different germ layers in most differentiation protocols. Thus, it is difficult to produce pure mono-lineage cultures of a desired cell type from PSCs (Murry and Keller, 2008). Finally, undifferentiated ESCs and iPSCs are tumorigenic and therefore, must be completely removed from their derivative tissues to be used for transplantation (Hentze et al., 2009).

It is an object of the present invention to provide culture and isolation methods that avoids these limitations.

SUMMARY OF THE INVENTION

In accordance with the present invention, a method is provided for the production of functional, non-tumorigenic, self-renewing endodermal progenitor (EP) cells. An exemplary method comprises contacting stem cells with Activin A in serum free differentiation medium thereby inducing formation of definite endoderm (DE) cells. The stem cells may be embryonic stem cells or induced pluripotent stem cells. The DE cells so produced are then cultured in a defined medium under low oxygen conditions in the presence of BMP4, VEGF, bFGF, and EGF on plates coated with a substrate and optionally a fibroblast feeder layer for a suitable period, thereby producing EP cells. In an alternative approach, the cells so treated can be incubated with a TGF-beta inducing agent, thereby producing EP cells. The EP cells so produced express SOX17, FOXA2, and HNF4A and lack OCT4 or NANOG expression. In a preferred embodiment of the culture methods described herein, EP cells are grown in a biocompatible matrix in the presence of mouse embryonic fibroblasts in a spinner flask as non adherent cells, thereby greatly increasing yields of EP cells so produced.

In yet another embodiment of the invention, the EP cells are induced to differentiate into endodermal tissues, which include for example, liver tissue, pancreatic tissue or intestinal tissue.

Pancreatic tissues produced using the methods of the invention are functionally responsive to chemical depolarization with KCl and also responsive to stimulation with D-glucose. Intestinal tissues produced exhibit CDX2, KLF5, and LYZ expression.

Figure 3:
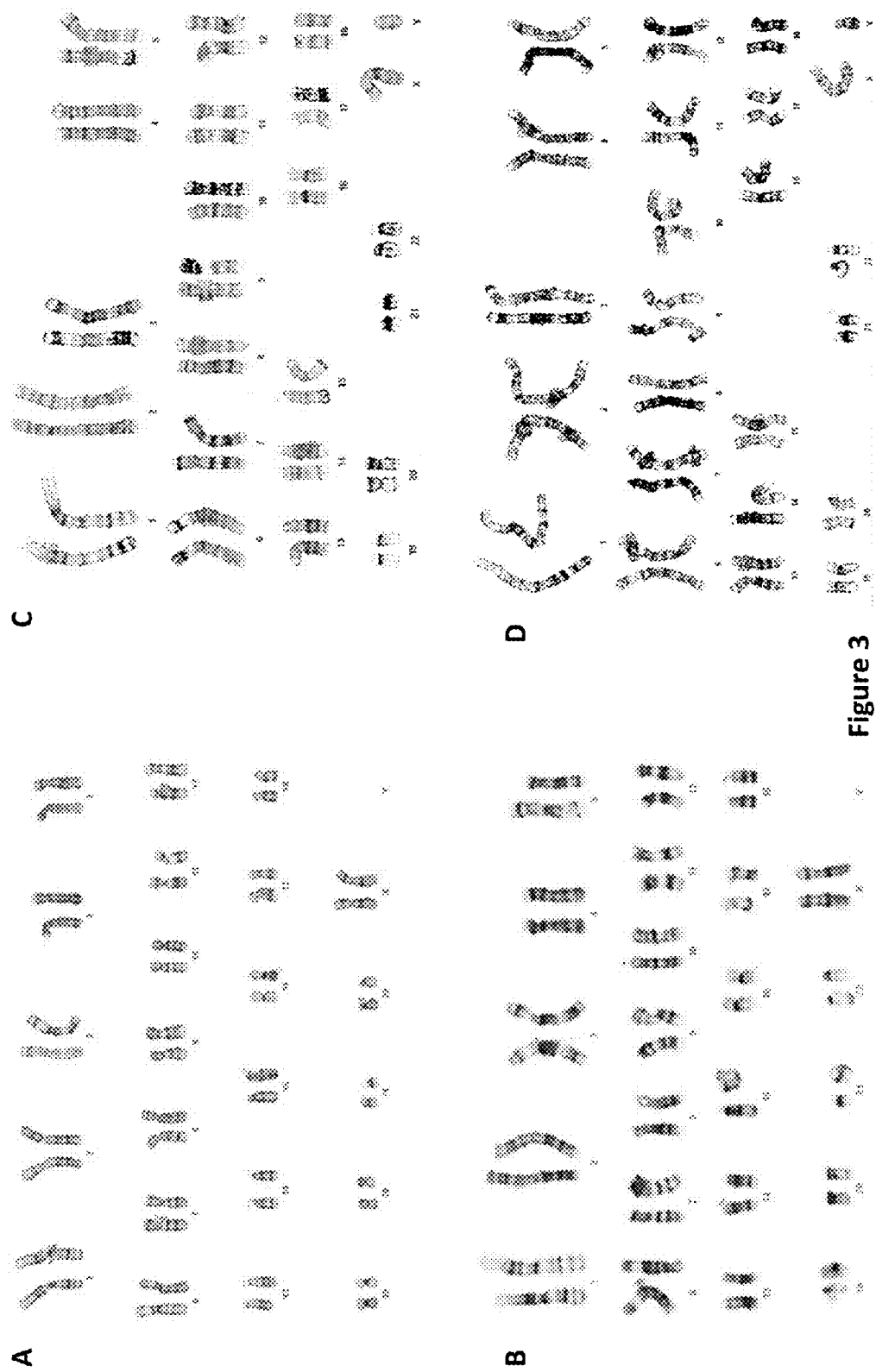

FIG. 3. Karyotype of EP cells. (A-B) Karyotypes of H9-EP cell line, passages 3 and 18. (C-D) Karyotypes of iPS2-derived EP cell line, passage 7 and 14.

Figure 4:
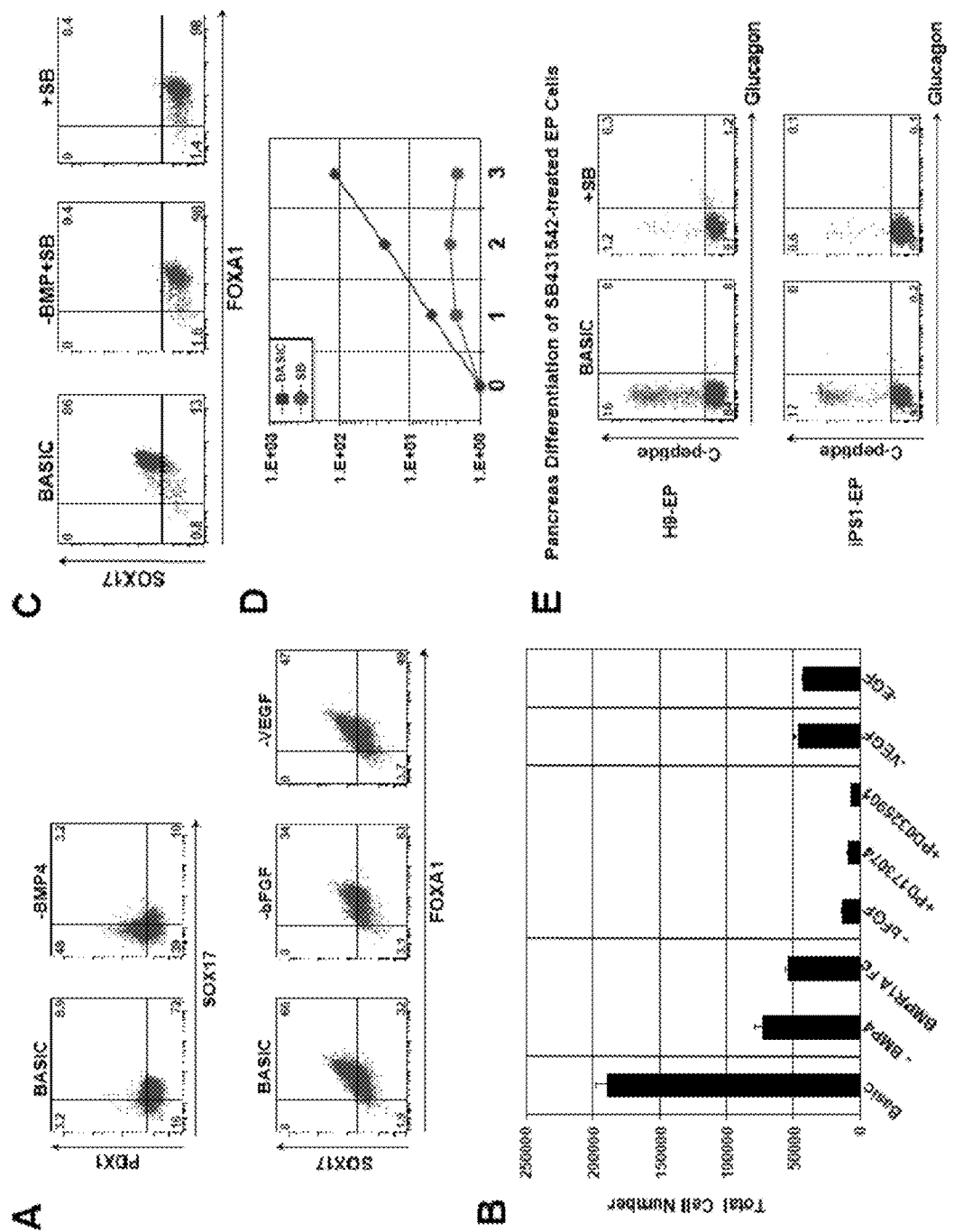

FIG. 4. Cytokine Requirements and Critical Signaling Pathways for EP Cell Maintenance and Differentiation. (A-B) To establish the requirement of BMP4, bFGF, VEGF and EGF in maintaining EP cells, $4\times10^4$ cells were cultured on matrigel with a MEF feeder layer in 12-well plates for a week in various media conditions as indicated. In each condition, one of the four cytokines was omitted or inhibitors of signaling pathways were added. The H9-EP cell line was grown for 1 week in optimal EP Basic Media (BASIC) or in the absence of BMP4, or bFGF or VEGF. (A) Flow cytometric analyses of SOX17 versus PDX1, or SOX17 versus FOXA1 are shown. (B) Graph shows total cell number of cells after 7-day expansion under various media conditions as indicated. − indicates withdrawal; + indicates addition. (C-D) To evaluate the role of TGF signaling in EP cell maintenance and differentiation, the small molecule inhibitor SB431542 was added to EP media. (C) H9-EP cells were cultured in normal EP media (BASIC) or in EP media supplemented with SB431542 (6 M) either in the presence (+SB) or the absence of BMP4 (−BMP+SB). Cells were harvested at day 6. Flow cytometric analyses of SOX17 versus FOXA1 are shown. (D) H9-EP cells were cultured in the presence (SB, red circles) or the absence (BASIC, blue squares) of SB431542 for 3 passages and cell growth analyzed by cell counts at each passage. Graph shows relative cell growth over time. (E) To assess the impact of TGF inhibition in EP cells upon pancreatic differentiation, H9-EP and iPS2-EP cells were cultured in the presence of SB431542 for 5 days, and were then differentiated into pancreas. Cells were harvested at day 14 of differentiation, and were compared to those derived from SB-untreated group (BASIC). Flow cytometric analyses of C-peptide versus Glucagon are shown.

Figure 5:
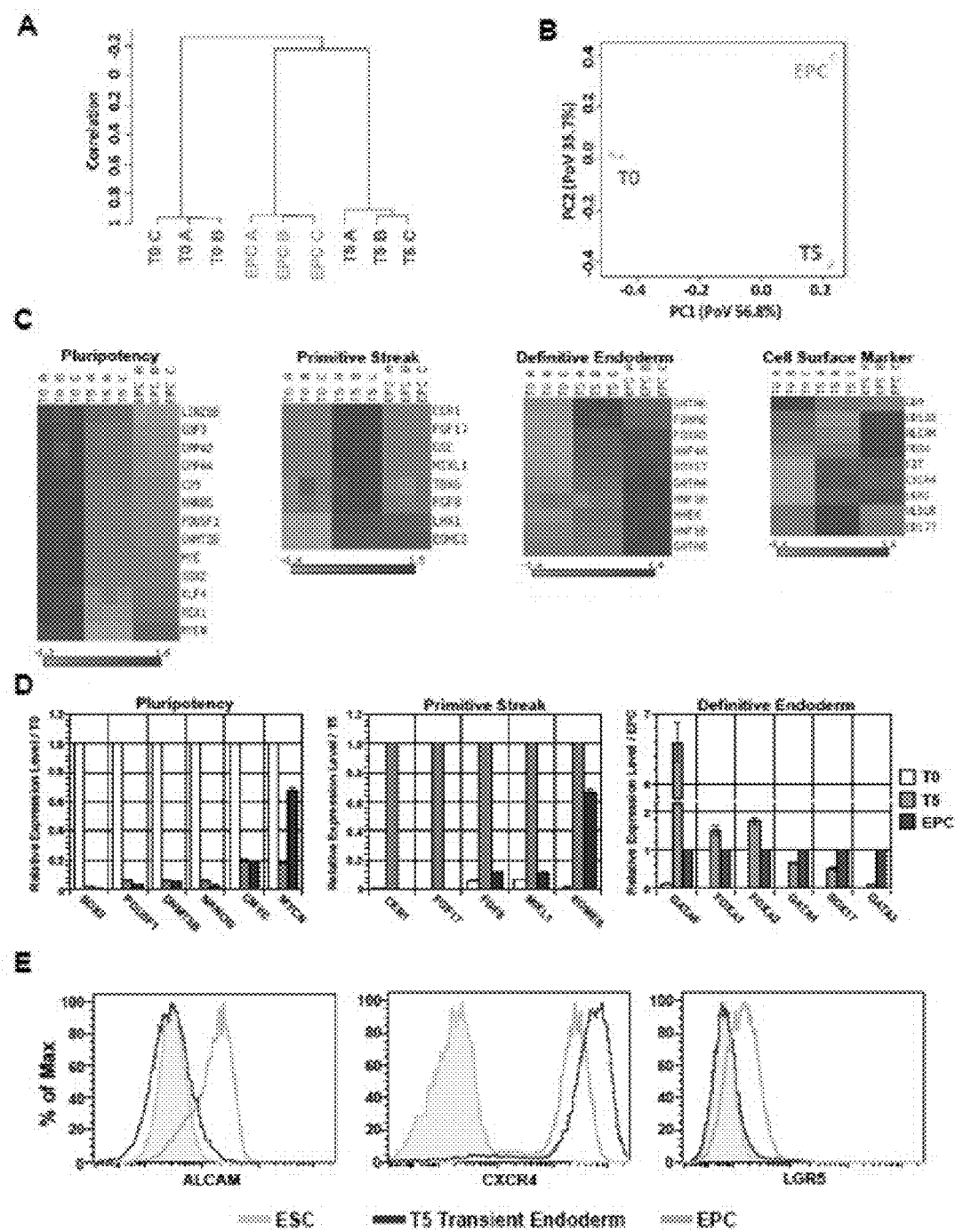

FIG. 5. Gene Expression Microarray Analyses of EP cells Compared to ESCs and Transient Definitive Endoderm. (A-C) Purified ESCs (sorted SSEA3$^{high}$ SSEA4$^{high}$), transient endoderm (day 5 high Activin treated, sorted CXCR4$^{high}$ CD117$^{high}$) and EP cells (sorted CXCR4$^{high}$ CD117$^{high}$) were analyzed using gene expression microarrays. Abbreviations—T0: ESCs; T5: transient endoderm; EPC: EP cells) (A) ESC, transient endodermal cell and EP cell global expression profile clustered by dendrogram. (B) Principal component analysis of populations in A. (C) Heat map expression levels of genes related to pluripotency, primitive streak/mesendoderm, definitive endoderm and cell surface markers. (D) Quantitative RT-PCR confirmation of a subset of genes examined in C. Expression levels were normalized to 1 in ESC for pluripotency genes, transient endoderm for primitive streak genes and EP cells for definitive endoderm genes, respectively. (E) Differential expression of a subset of the cell surface markers predicted by the microarray studies was confirmed by flow cytometry on ESCs, EP cells and day 5 endoderm, demonstrating that ALCAM and LGR5 are enriched on EP cells.

Figure 6:
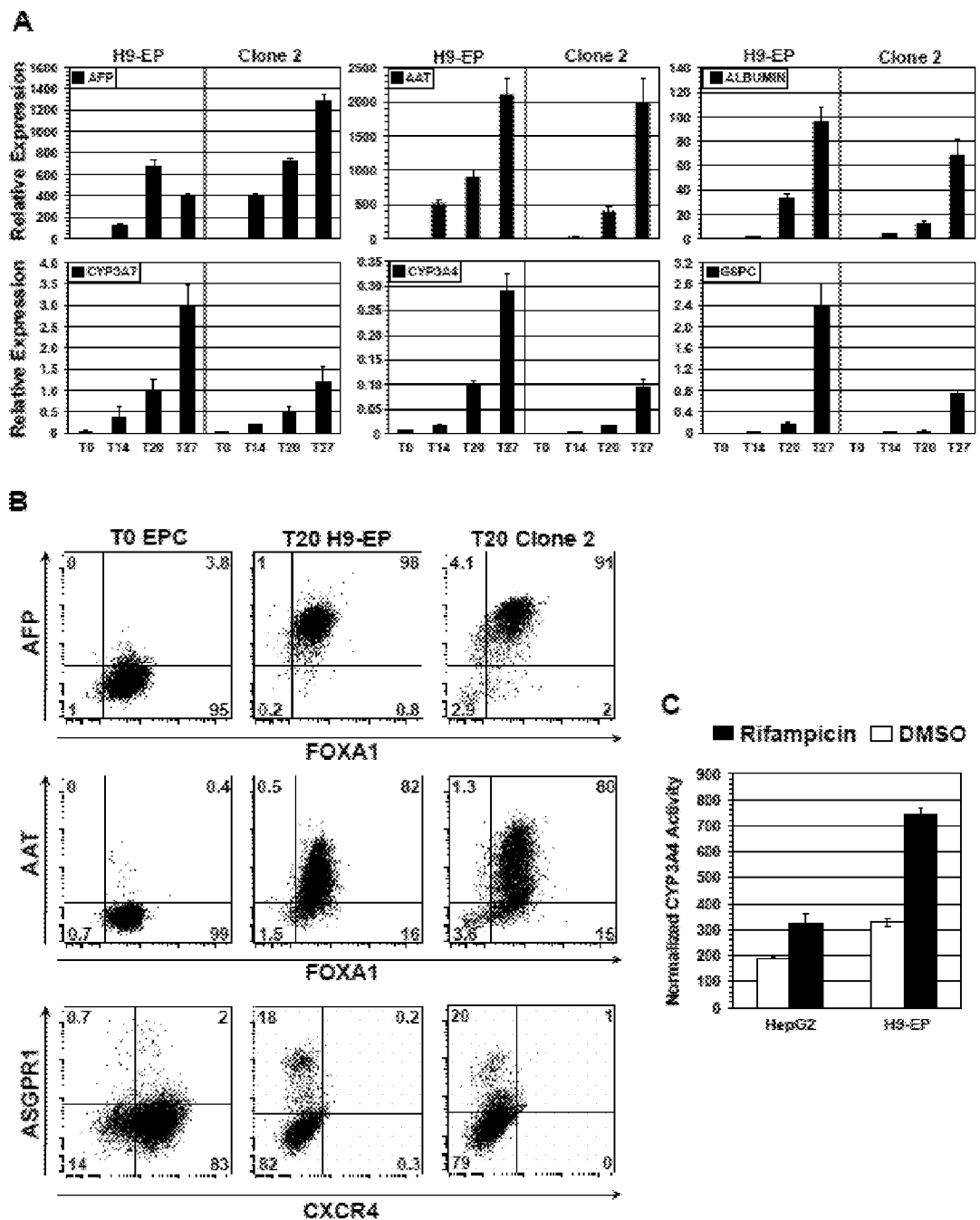

FIG. 6. Hepatic Differentiation of Endodermal Progenitor Cells in vitro. (A-C) Cells from the H9-EP line and from one single cell-derived sub-clone (Clone 2) were differentiated into hepatocytes as indicated, and were harvested for analyses at days 14, 20, and 27 (T14, T20 and T27). (A) Gene expression was analyzed by QRT-PCR on samples harvested at three time points from H9-EP and Clone 2 lines, comparing to undifferentiated EP cells (T0). The expression of indicated genes is normalized to the housekeeping gene CYCLOPHILIN. Values represent the mean of three independent differentiation experiments. Error bars represent the standard error. (B) Flow cytometry analyses of AFP versus FOXA1, AAT versus FOXA1 or ASGPR1 versus CXCR4 at day 20 of differentiation, comparing to undifferentiated EP cells (T0 EPC). Percentage of cells within each quadrant is indicated. Shown are the representative data from H9-EP (passage 10) and Clone 2 EP (passage 6) cells. (C) To assess CYP3A4 activity of EP cell-derived hepatocytes, H9-EP cells (passage 15) were differentiated into hepatocytes for 24 days and then cultured in the presence (Rifampicin) or absence (DMSO) of Rifampicin for 3 days, and compared to HepG2 cells. Values represent means of measured luminescence units normalized to $6\times10^4$ cells, and error bars represent SE (n=3).

Figure 7:
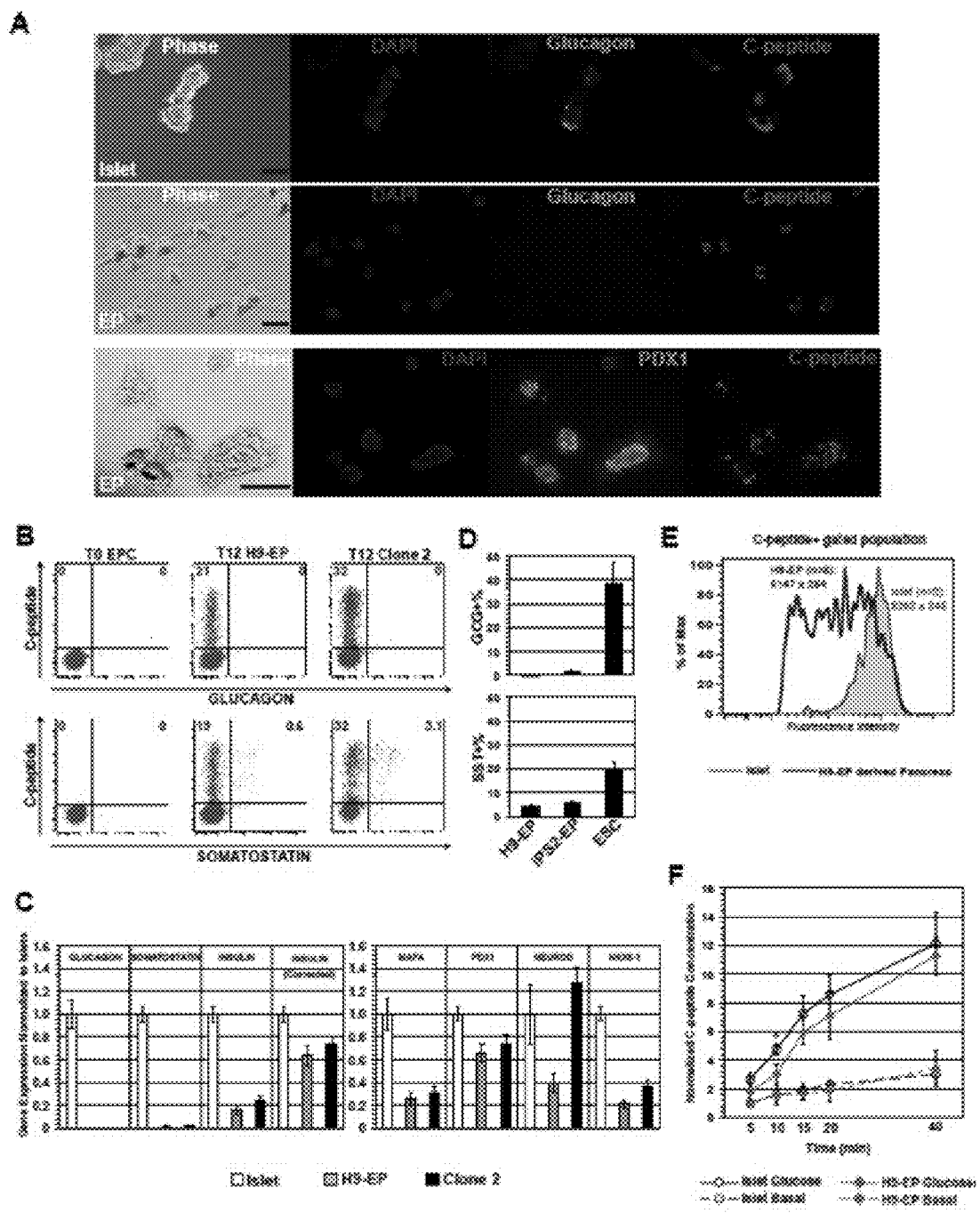

FIG. 7. Pancreatic Differentiation of Endodermal Progenitor Cells In Vitro. (A-D) Cells from the H9-EP cell line (passages 6-12) and from one single cell-derived sub-clone (clone 2) (passages 5-11) were differentiated into pancreatic cells as indicated in the text. Cells were harvested for analyses at day 12 (T12) to day 18. (A) Immuno-fluorescence staining of human islets (Islet) and day 14 EP-cell derived pancreatic cultures (EP) for c-peptide (red) and Glucagon (green) or PDX1 (green). Scale bars represent 100 um. (B) Intracellular flow cytometric analyses of C-peptide versus GLUCAGON and c-peptide versus SOMATOSTATIN at day 12 of differentiation. (C) Gene expression was analyzed by QRT-PCR on samples harvested at day 18 of differentiation and compared to adult islets. The expression of indicated genes is normalized to 1 in islets. Values represent the mean of three independent differentiation experiments or two batches of adult islets. Error bars represent the standard error. (D) The percentage of c-peptide+ cells that co-express either SST or GCG was quantified. Data are shown for endocrine cells generated from EP cells (H9-EP, n=12; and iPS2-EP, n=5) and directly from H9 ESCs (ESC, n=4). (E) Intracellular flow cytometric analyses of c-peptide expression, gated on c-peptide+ cells from day 12 EP cell-derived pancreatic cultures (blue histogram) and from human islets (red filled histogram). The values shown are mean fluorescence intensity of c-peptide in H9-EP derived cells (blue, n=6) and human islets (red, n=2). (F) The H9-EP cells were differentiated into β-cells and stimulated with D-glucose at 2 mM (Basal) or 20 mM (Glucose) at day 14, and were compared to adult islets. C-peptide release was measured at various time points (5, 10, 15, 20 and 40 minutes) (H9-EP, n=3; islets, n=2; error bars represent the standard error). Asterisk indicates statistical significance as determined by t-test, P=0.022).

Figure 8:
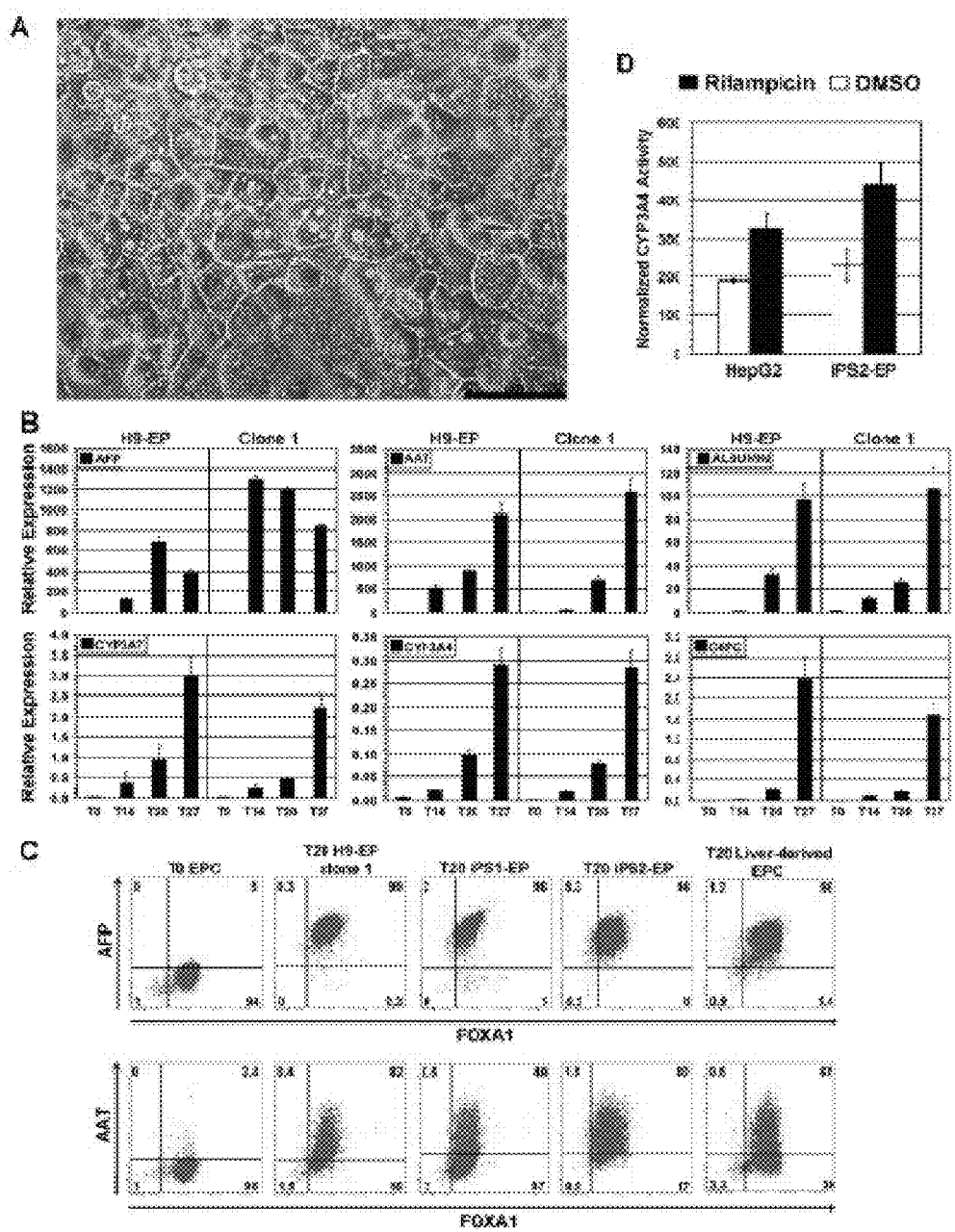

FIG. 8. Hepatic Differentiation of Various EP Cell Lines. (A) Phase contrast image of day 20 hepatic differentiation cultures of H9-EP cells, captured using 20× objective, scale bar=100 m. (B) Gene expression was analyzed by QRT-PCR on samples harvested at three time points from two EP cell lines (H9-EP and clone 1), compared to undifferentiated EP cells (T0). The expression of indicated genes is normalized to the housekeeping gene PPIG. Values represent the mean of three independent differentiation experiments. Error bars represent the standard error. (C) Flow cytometry analyses of AFP versus FOXA1, and AAT versus FOXA1 at day 20 of differentiation from H9-EP Clone 1, and from two iPS-EP (iPS1 and iPS2) and Liver-derived EP cell lines (passage 8, passage 7, passage 15 and passage 10, respectively), compared to undifferentiated EP cells (T0 EPC). Percentage of cells within each quadrant is indicated. (D) To assess CYP3A4 activity of EP cell-derived hepatocytes, iPS2-EP cells (passage 12) were differentiated into hepatocytes for 24 days and then cultured in the presence (Rifampicin) or the absence (DMSO) of Rifampicin for 3 days, and were compared to HepG2 cells. Values represent means of measured luminescence units normalized to $6\times10^4$ cells, and error bars represent SE (n=3 independent experiments).

Figure 9:
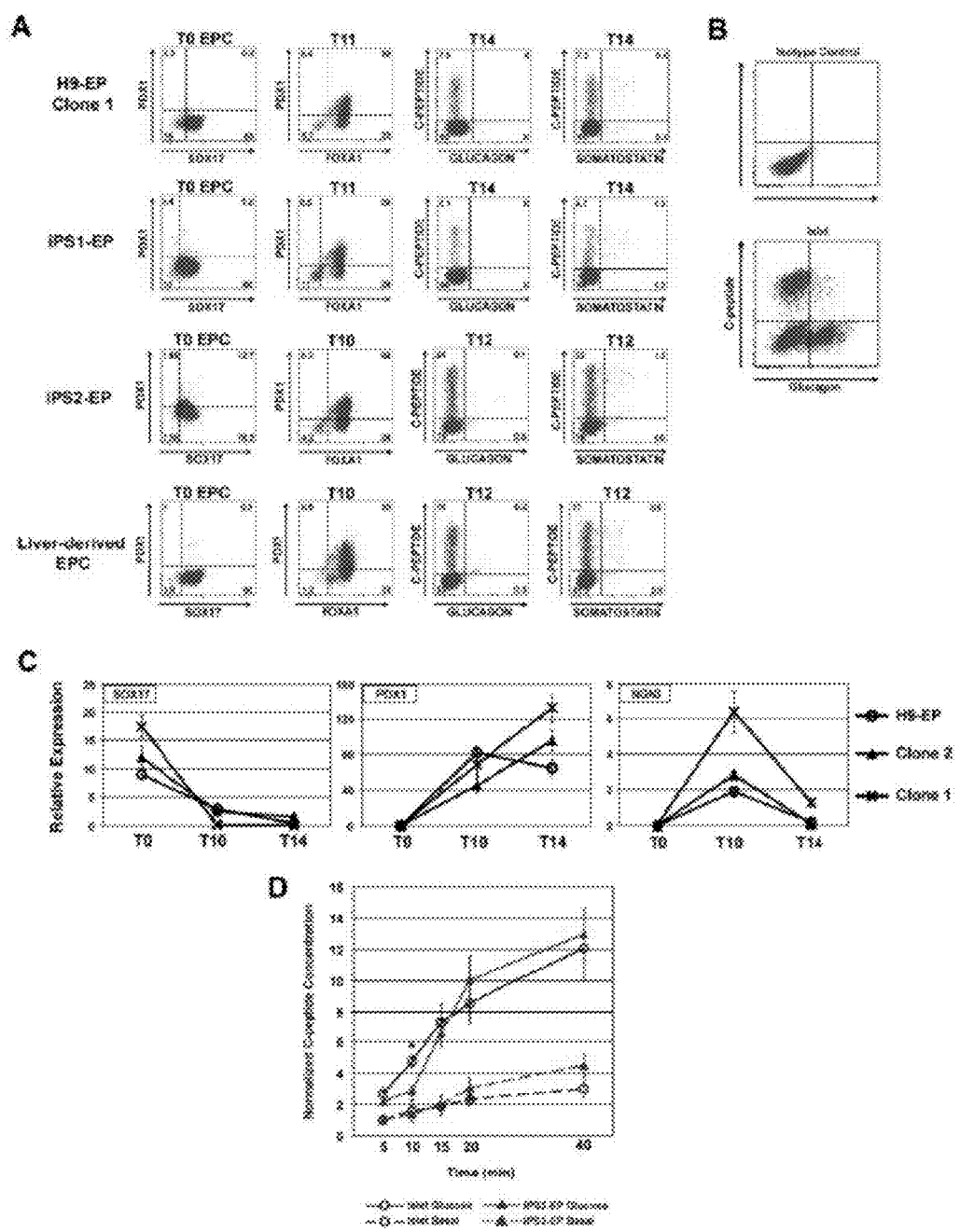

FIG. 9. Pancreatic Differentiation of Various EP Cell Lines In Vitro. Cells from H9Clone 1, iPS1-EP, iPS2-EP and Liver-derived EP cell lines (passage 8, passage 7, passage 12 and passage 10, respectively) were differentiated into pancreatic cells as indicated in the text. Cells were harvested for analyses between day 10 (T10) and day 14 (T18). (A) Intracellular flow cytometry analyses of PDX1 versus SOX17, PDXlversus FOXA1, c-peptide versus GLUCAGON and c-peptide versus SOMATOSTATIN at days 10 to 14 of differentiation, compared to undifferentiated EP cells (T0 EPC). Percentage of cells within each quadrant is indicated. (B) Intracellular flow cytometry analysis of adult islets for C-peptide versus GLUCAGON and isotype control antibodies. (C) Kinetics of gene expression. Gene expression was analyzed by QRT-PCR on H9-EP, clone 1 and clone 2 samples harvested at days 10 and 14 of differentiation, compared to undifferentiated EP cells (T0). The expression of indicated genes is normalized to the housekeeping gene PRIG. Values represent the mean of four independent differentiation experiments. Error bars represent the standard error. (D) iPS2-EP cells were differentiated into beta cells and stimulated with D-glucose at 2 mM (Basal) or 20 mM (Glucose) at day 14, and then compared to adult islets. C-peptide release was measured at various time points (5, 10, 15, 20 and 40 min)(iPS2-EP, n=3; adult islets, n=2; error bars represent the standard error). Asterisk indicates statistical significance as determined by t-test, P=0.023.

Figure 10:
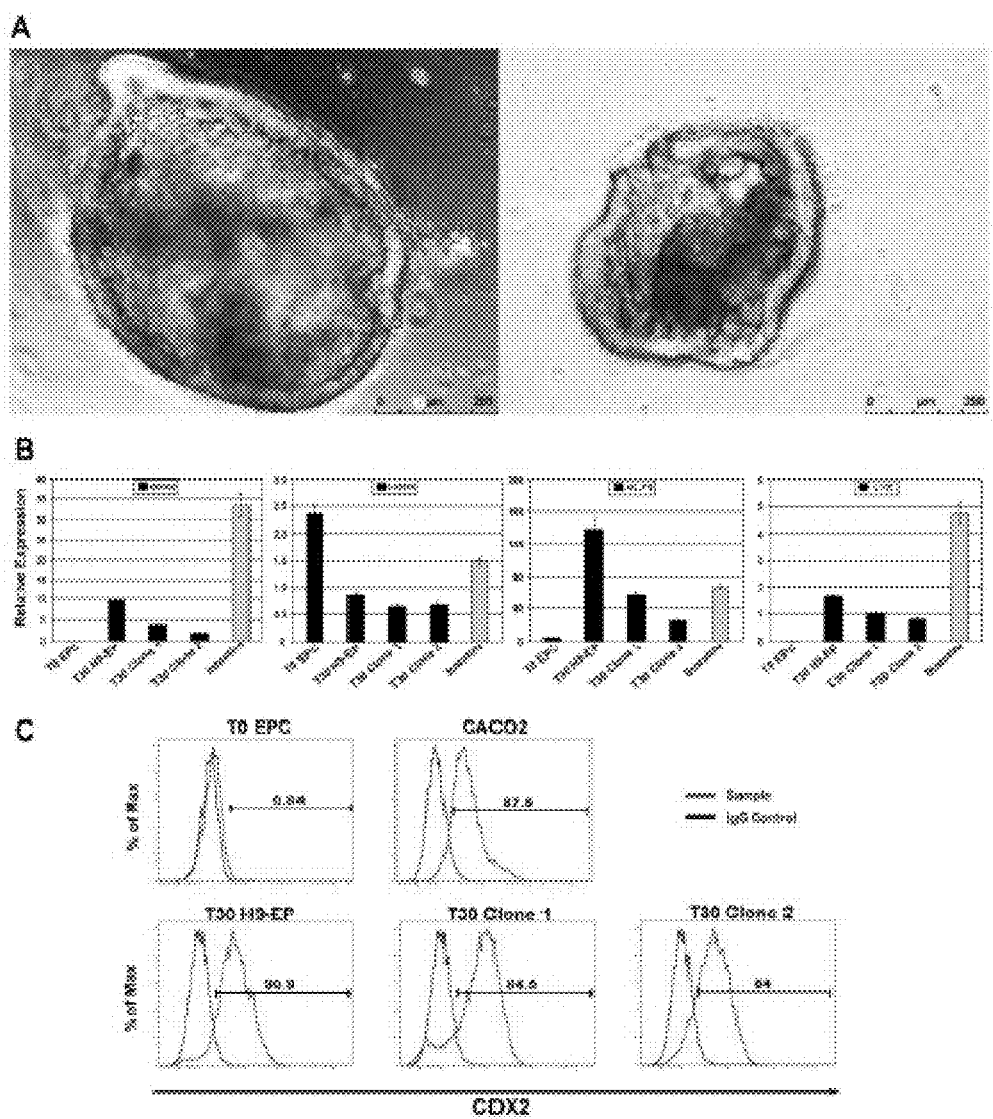

FIG. 10. Intestinal Differentiation of Endodermal Progenitor Cells In Vitro. Cells from the H9-EP line (Passages 6, 9 and 12) and from the two single cell-derived sub-clones (Clone 1, passages 6, 7 and 9; Clone 2, passages 5, 6 and 8) were differentiated into intestinal organoids and harvested at day 30. (A) Phase contrast images showing typical intestinal organoid morphology at day 30 of culture, captured using 20× objective. (B) Gene expression was analyzed by QRT-PCR on (H9-EP, Clone 1 and Clone 2), comparing to undifferentiated EP cells (T0 EPC) and adult intestinal cDNAs. The expression of indicated genes is normalized to the housekeeping gene PPIG. Values represent the mean of three independent differentiation experiments. Error bars represent the standard errors. (C) Intracellular flow cytometry analyses for CDX2 at day 30 of differentiation, comparing to undifferentiated EP cells (T0 EPC) and human intestinal tumor cell lines CACO2. Percentage of positive cells is indicated.

Figure 11:
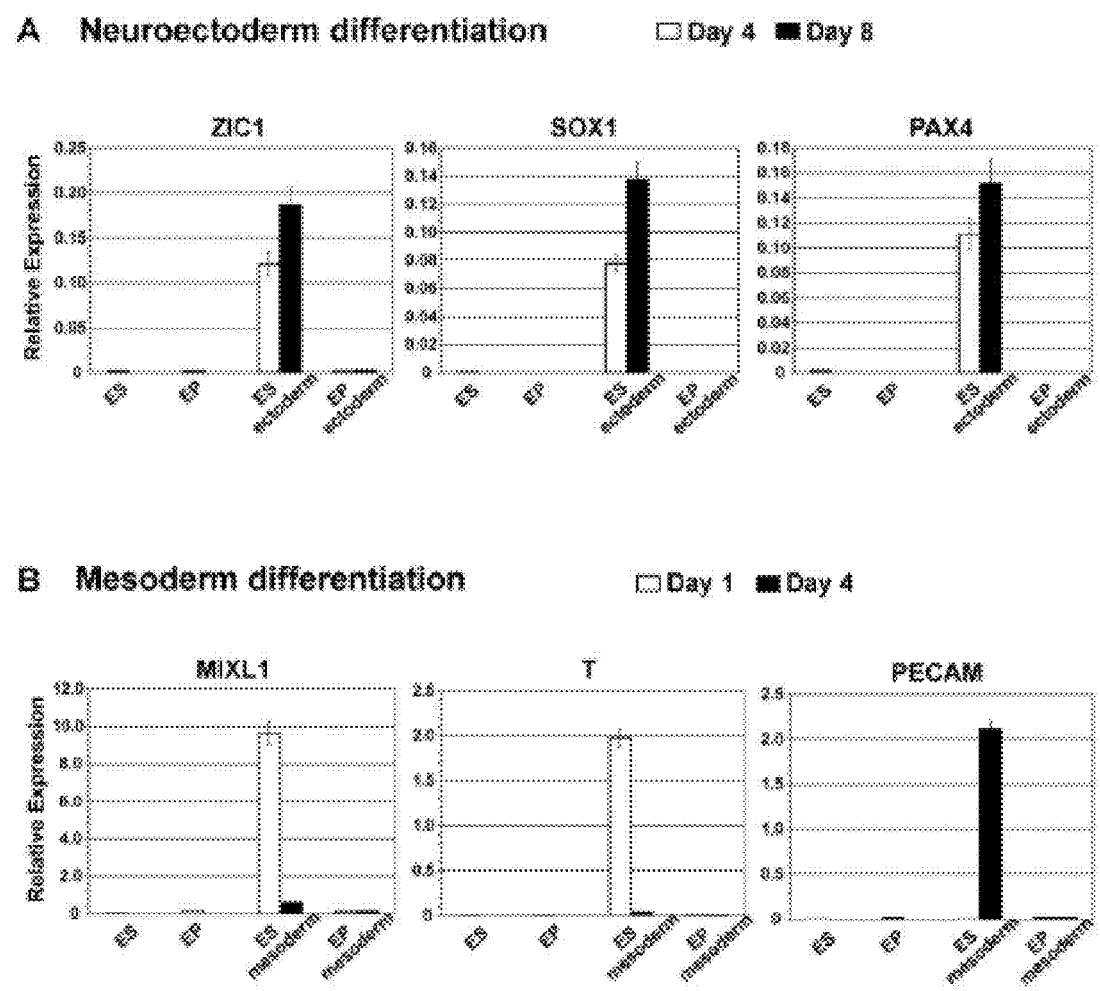

FIG. 11. Neuroectoderm and Mesoderm Induction of EP Cells. To evaluate the latent potential of EP cells to differentiate into neuroectoderm or mesoderm, H9-EP cells (passage 5) and H9 ESCs were induced with conditions established for promoting hESC differentiation towards either neuroectoderm or mesoderm. Gene expression was analyzed by QRT-PCR on samples harvested at two time points (days 4 and 8 for neuroectoderm differentiation; days 1 and 4 for mesoderm differentiation), and were compared to undifferentiated ES (ES) and EP (EP) cells. The expression of indicated genes is normalized to the housekeeping gene PPIG. Values represent the mean of three independent differentiation experiments. Error bars represent the standard error.

Figure 12:
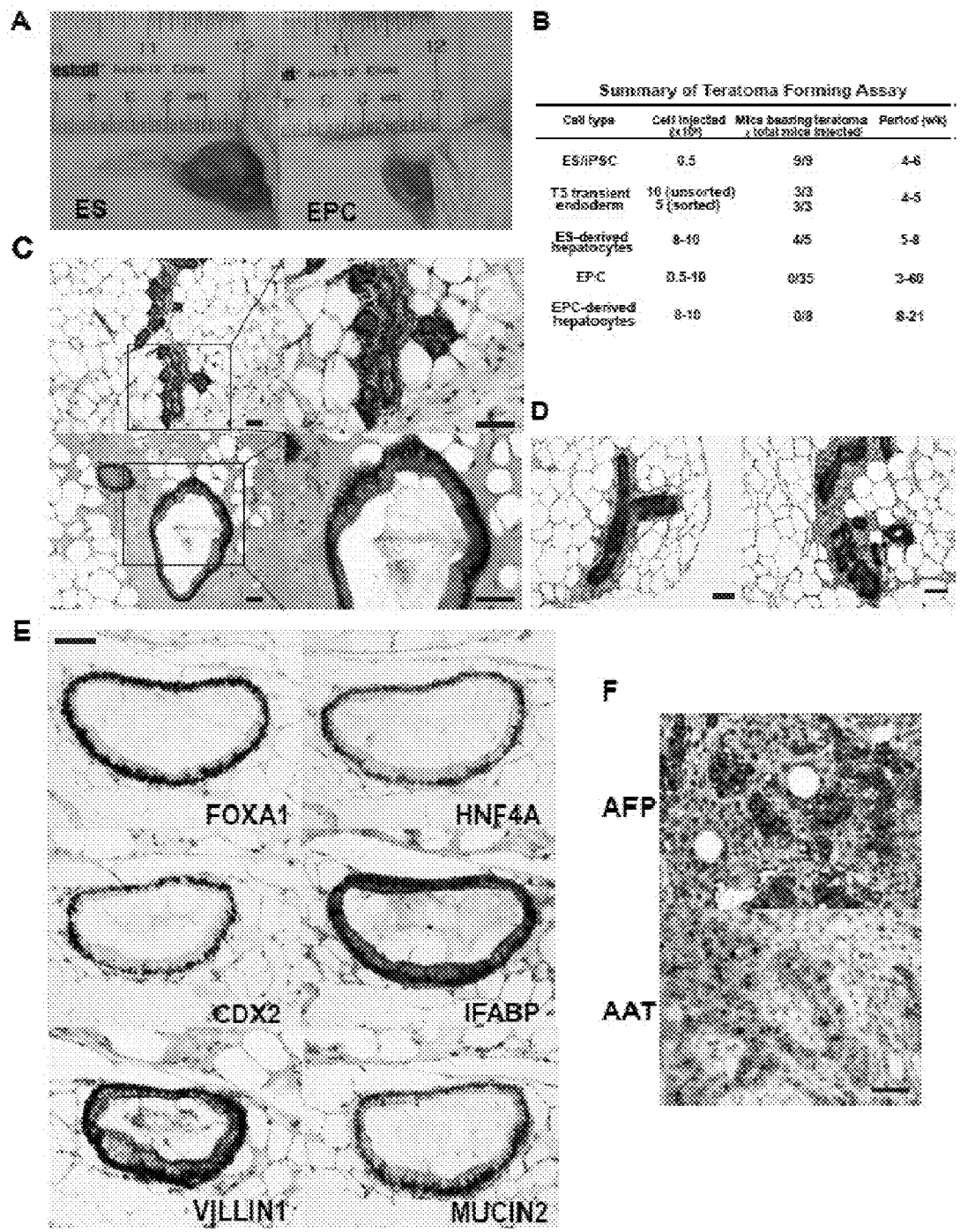

FIG. 12. Tumor Potential and Spontaneous Differentiation of Endoderm Progenitor Cells in vivo. (A) To determine if EP cells retain teratoma forming potential, 0.5 million H9 ESCs or H9-EP cells were transplanted intramuscularly into immune compromised mice. Images show teratoma formation in a mouse injected with ESCs (ES, left panel) and lack of tumor formation in a mouse injected with EP cells (EP, right panel). (B) A summary of teratoma-forming ability of pluripotent stem cells (ES/iPSC), day 5 (T5) transient endoderm, ESC-derived day 20 hepatocyte cultures (ES-derived hepatocytes); EP cells (EPC) and EP cell-derived day 9 hepatocyte cultures (EPC-derived hepatocytes). For transient endoderm, both bulk cultures and CXCR4+CD117high sorted cells were used for transplantation. (C—F) Analyses of EP cell transplants. 8 to 10 million EP cells mixed with matrigel were injected subcutaneously into immune deficient mice, and the resultant matrigel plugs were isolated 3-12 weeks post-transplantation. Scale bars represent 100 um. (C) Sections of matrigel plugs were stained with hematoxylin and eosin. Shown are endoderm-like structures at lower (10×, left panel) and higher magnifications (20×, right panel). (D) Immunohistochemistry using an anti-human antibody reveals human cell-derived endodermal structures surrounded by non-human mesenchyme and adipocytes. (E) Immunohistochemistry for intestinal markers reveals gut/intestinal structures in the matrigel plug. (F) Immunohistochemistry for hepatocyte markers in the matrigel plug.

Figure 13:
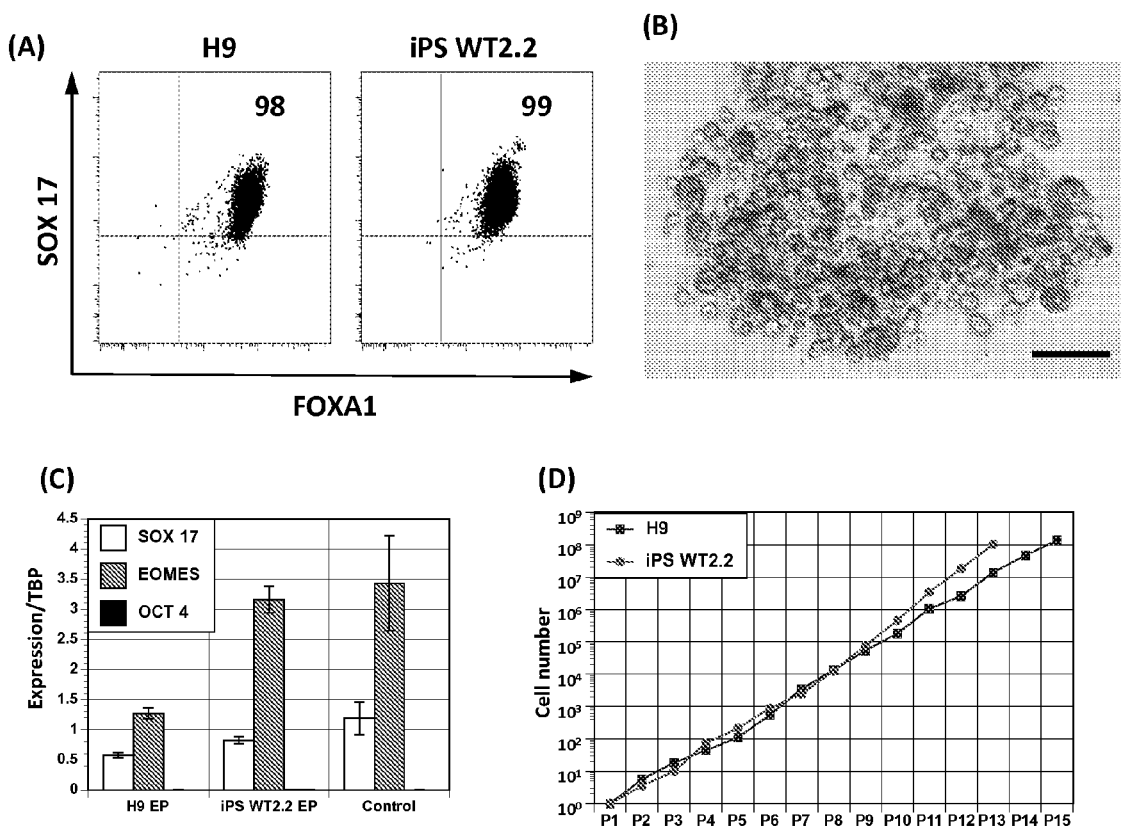

FIG. 13: Expansion of EP cells in spinner flask bioreactor culture. EP cells were generated from H9 ES cells and WT2.2 iPS cells were expanded in bioreactor culture for 13-15 passages. (A) Intracellular flow cytometry for FOXA1 vs. SOX17 for H9 (passage 15) and WT2.2 (passage 13) EP cell lines. (B) H9 EP cell cultures were examined by microscopy at passage 15 (day 4) in spinner flask culture. Bar is 200 um. (C) Gene expression analysis by QRT-PCR of the endodermal markers SOX17 and EOMES and the ES cell marker OCT4. H9 and WT2.2 EP cell lines expanded in spinner flask culture were compared to EP cells grown in adherent culture (control). Data shown is relative to the housekeeping gene TBP. (D) Growth curve for H9 derived and iPS cell derived EP cell line in spinner flask culture.

Figure 14:
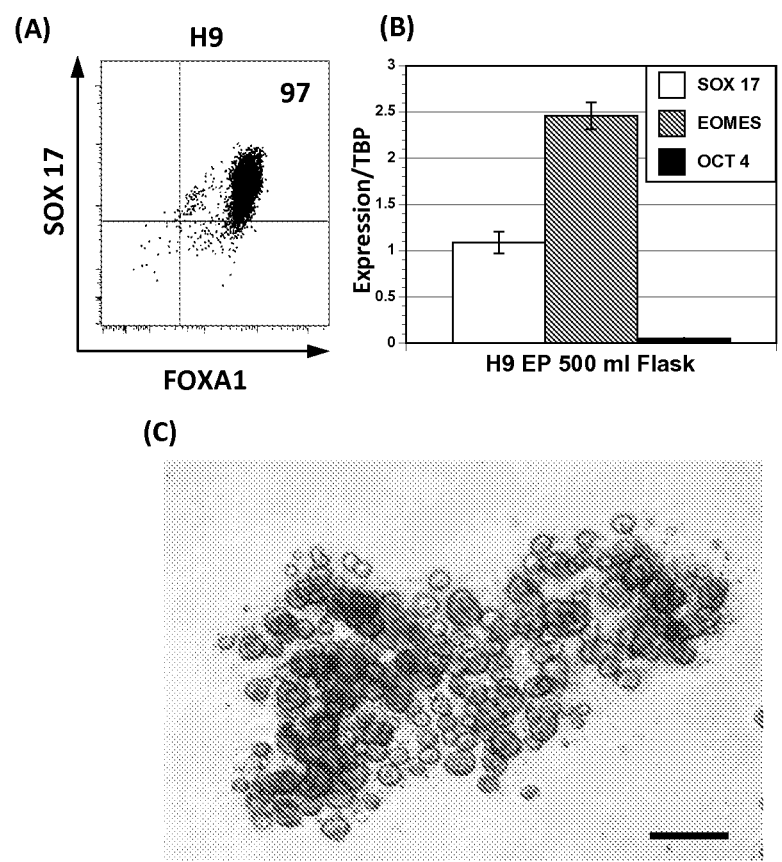

FIG. 14: Expansion of EP cells in 500 ml spinner flask bioreactor culture. EP cells were generated from H9 ES cells were expanded in 500 ml spinner flask for 2 passages. (A) Intracellular flow cytometry for FOXA1 vs. SOX17. (B) Gene expression analysis by QRT-PCR of the endodermal markers SOX17 and EOMES and the ES cell marker OCT4. H9 EP cell lines expanded 2 passages in 500 ml spinner flask culture were examined. Data shown is relative to the housekeeping gene TBP. (C) H9 EP cell cultures were examined by microscopy at passage 2 (day 6) in 500 ml spinner flask culture. Bar is 200 um.

Figure 15:
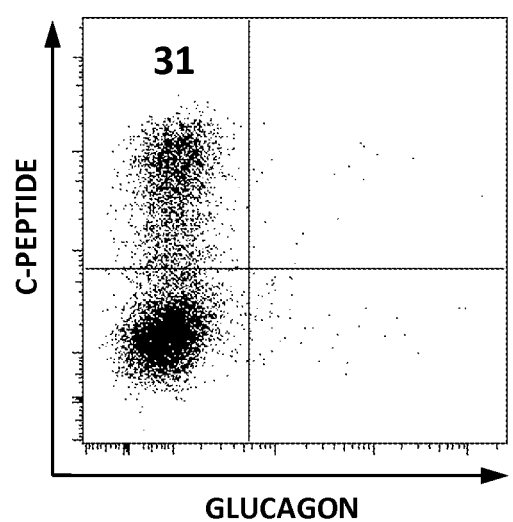

FIG. 15: EP cells expanded in spinner flask bioreactor culture still generate pancreatic beta cells. EP cells expanded for >10 passages in spinner flask were differentiated into pancreatic beta like cells. Intracellular flow cytometry of Glucagon vs C-peptide is shown.

DETAILED DESCRIPTION OF THE INVENTION

The use of human pluripotent stem cells for laboratory studies and cell-based therapies is hampered by tumor forming potential and limited ability to generate pure populations of differentiated cell types in vitro. To address these issues, we established endodermal progenitor (EP) cell lines from human embryonic and induced pluripotent stem cells. Optimized growth conditions were established that allow near unlimited ($>10^{16}$) EP cell self-renewal while displaying a morphology and gene expression pattern characteristic of definitive endoderm. Upon manipulation of culture conditions in vitro or transplantation into mice, clonally-derived EP cells differentiate into numerous endodermal lineages including mono-hormonal gluco-seresponsive pancreatic beta cells, hepatocytes and intestinal epithelia. Importantly, EP cells are non-tumorigenic in vivo.

Human embryonic stem cells (ESCs) and induced pluripotent stem cells (iPSCs) offer tremendous potential for both basic biology and cell based therapies for a wide variety of diseases due to their ability to be expanded in vitro along with their potential to differentiate into any cell type in the body. Differentiation of ES/iPS cells appears to mimic the process of development that occurs during embryogenesis. These stem cell populations proceed down developmental intermediaries with successively restricted potential until mature cell types are generated. First the primary germ layers are formed, mesoderm, endoderm, and ectoderm, that then further mature into derivative cell types. Two endodermal derived tissue types that are especially appealing for stem cell replacement therapies are β cells of the pancreatic islet and hepatocytes to treat type I diabetes and liver disease respectively. Currently, there is a critical shortage of both islets and livers for use in transplant settings. For human ESCs or iPSCs to be utilized for cellular therapies two hurdles need to be overcome: (1) Safety issues due to tumor formation from ESCs/iPSCs. Even a small contamination of undifferentiated ESCs or iPSCs in the transplanted tissue runs the risk of tumor formation. (2) The ability to generate mature functional tissue types for transplant is currently limited due to the necessity to differentiate ESCs through all stages of development.

To address both of these issues, we have defined culture conditions that can generate self-renewing endoderm progenitor (EP) cell lines from human ESCs and iPSCs. First, ESCs or iPSCs are induced to form definitive endoderm via treatment with Activin A in defined serum free media. The definitive endoderm cells are then grown in low oxygen conditions with BMP4, VEGF, bFGF, and EGF on a matrigel coated plates in serum free media. Using these conditions, EP cells can be established and maintained in culture for at least several months with a proliferative potential of >10 million fold. These lines are similar to ESCs in that they can be expanded in vitro and differentiate into endodermal cell types. These cells express markers indicative of endoderm differentiation such as SOX17, FOXA2, and HNF4A while they do not express genes typically found in ESCs or iPSCs such as OCT4 or NANOG. In addition, EP cells do not have the tumor forming ability that ESCs or iPSCs do when transplanted into immune deficient mice. The induction of mature endodermal tissues from EP cells should be more efficient as EP cells have already been specified to the endodermal germ layer and are thus, developmentally closer to mature endodermal-derived tissue types such as pancreas or liver. We have shown that EP cells have the ability to generate hepatocytes and pancreatic cells in vitro. These cell lines will serve as an excellent source of starting material to study the inductive signals necessary for the specification of mature endodermal-derived cell types.

To summarize, we have found the culture conditions to generate EP cells that have the advantage of ES cells or iPS cells in that they can be expanded in culture and differentiated into endoderm derived cell types while lacking the tumor forming potential of ES or iPS cells obtained using methods in the prior art. As EP cells can be produced from any ESC or iPSC line, generation of patient or disease specific EP cell lines should be straight forward an offer a more robust platform for drug testing and as a source of tissue for cellular therapies.

The following definitions are provided to facilitate an understanding of the present invention:

"Multipotent" implies that a cell is capable, through its progeny, of giving rise to several different cell types found in the adult animal.

"Pluripotent" implies that a cell is capable, through its progeny, of giving rise to all the cell types which comprise the adult animal including the germ cells. Both embryonic stem and embryonic germ cells are pluripotent cells under this definition.

The term "autologous cells" as used herein refers to donor cells which are genetically compatible with the recipient.

The term "totipotent" as used herein can refer to a cell that gives rise to a live born animal. The term "totipotent" can also refer to a cell that gives rise to all of the cells in a particular animal. A totipotent cell can give rise to all of the cells of an animal when it is utilized in a procedure for developing an embryo from one or more nuclear transfer steps. Totipotent cells may also be used to generate incomplete animals such as those useful for organ harvesting, e.g., having genetic modifications to eliminate growth of an organ or appendage by manipulation of a homeotic gene. Additionally, genetic modification rendering oocytes, such as those derived from ES cells, incapable of development in utero would ensure that human derived ES cells could not be used to derive human oocytes for reproduction and only for applications such as therapeutic cloning.

The term "cultured" as used herein in reference to cells can refer to one or more cells that are undergoing cell division or not undergoing cell division in an in vitro environment. An in vitro environment can be any medium known in the art that is suitable for maintaining cells in vitro, such as suitable liquid media or agar, for example. Specific examples of suitable in vitro environments for cell cultures are described in Culture of Animal Cells: a manual of basic techniques (3.sup.rd edition), 1994, R. I. Freshney (ed.), Wiley-Liss, Inc.; Cells: a laboratory manual (vol. 1), 1998, D. L. Spector, R. D. Goldman, L. A. Leinwand (eds.), Cold Spring Harbor Laboratory Press; and Animal Cells: culture and media, 1994, D. C. Darling, S. J. Morgan John Wiley and Sons, Ltd.

The term "cell line" as used herein can refer to cultured cells that can be passaged at least one time without terminating. The invention relates to cell lines that can be passaged indefinitely. Cell passaging is defined hereafter.

The term "suspension" as used herein can refer to cell culture conditions in which cells are not attached to a solid support. Cells proliferating in suspension can be stirred while proliferating using apparatus well known to those skilled in the art.

The term "monolayer" as used herein can refer to cells that are attached to a solid support while proliferating in suitable culture conditions. A small portion of cells proliferating in a monolayer under suitable growth conditions may be attached to cells in the monolayer but not to the solid support.

The term "plated" or "plating" as used herein in reference to cells can refer to establishing cell cultures in vitro. For example, cells can be diluted in cell culture media and then added to a cell culture plate, dish, or flask. Cell culture plates are commonly known to a person of ordinary skill in the art. Cells may be plated at a variety of concentrations and/or cell densities.

The term "cell plating" can also extend to the term "cell passaging." Cells of the invention can be passaged using cell culture techniques well known to those skilled in the art. The term "cell passaging" can refer to a technique that involves the steps of (1) releasing cells from a solid support or substrate and disassociation of these cells, and (2) diluting the cells in media suitable for further cell proliferation. Cell passaging may also refer to removing a portion of liquid medium containing cultured cells and adding liquid medium to the original culture vessel to dilute the cells and allow further cell proliferation. In addition, cells may also be added to a new culture vessel which has been supplemented with medium suitable for further cell proliferation.

The term "biocompatible matrix" refers to composition know to support and be conducive to cell culture and differentiation. Exemplary compositions include, without limitation, matrigel and GelTrex (Life Technologies).

The term "proliferation" as used herein in reference to cells can refer to a group of cells that can increase in number over a period of time.

The term "permanent" or "immortalized" as used herein in reference to cells can refer to cells that may undergo cell division and double in cell numbers while cultured in an in vitro environment a multiple number of times until the cells terminate. A permanent cell line may double over 10 times before a significant number of cells terminate in culture. Preferably, a permanent cell line may double over 20 times or over 30 times before a significant number of cells terminate in culture. More preferably, a permanent cell line may double over 40 times or 50 times before a significant number of cells terminate in culture. Most preferably, a permanent cell line may double over 60 times before a significant number of cells die in culture.

The term "reprogramming" or "reprogrammed" as used herein may refer to materials and methods that can convert a cell into another cell having at least one differing characteristic.

The term "isolated" as used herein can refer to a cell that is mechanically separated from another group of cells. Examples of a group of cells are a developing cell mass, a cell culture, a cell line, and an animal.

The term "embryonic stem cell" as used herein can refer to pluripotent cells isolated from an embryo that are maintained in in vitro cell culture. Such cells are rapidly dividing cultured cells isolated from cultured embryos which retain in culture the ability to give rise, in vivo, to all the cell types which comprise the adult animal, including the germ cells. Embryonic stem cells may be cultured with or without feeder cells. Embryonic stem cells can be established from embryonic cells isolated from embryos at any stage of development, including blastocyst stage embryos and pre-blastocyst stage embryos. Embryonic stem cells may have a rounded cell morphology and may grow in rounded cell clumps on feeder layers. Embryonic stem cells are well known to a person of ordinary skill in the art. See, e.g., WO 97/37009, entitled "Cultured Inner Cell Mass Cell-Lines Derived from Ungulate Embryos," Stice and Golueke, published Oct. 9, 1997, and Yang & Anderson, 1992, Theriogenology 38: 315-335. See, e.g., Piedrahita et al. (1998) Biol. Reprod. 58: 1321-1329; Wianny et al. (1997) Biol. Reprod. 57: 756-764; Moore & Piedrahita (1997) In Vitro Cell Biol. Anim. 33: 62-71; Moore, & Piedrahita, (1996) Mol. Reprod. Dev. 45: 139-144; Wheeler (1994) Reprod. Fert. Dev. 6: 563-568; Hochereau-de Reviers & Perreau, Reprod. Nutr. Dev. 33: 475-493; Strojek et al., (1990) Theriogenology 33: 901-903; Piedrahita et al., (1990) Theriogenology 34: 879-901; and Evans et al., (1990) Theriogenology 33: 125-129.

The term "differentiated cell" as used herein can refer to a precursor cell that has developed from an unspecialized phenotype to a specialized phenotype. For example, embryonic cells can differentiate into an epithelial cell lining the intestine. Materials and methods of the invention can reprogram differentiated cells into totipotent cells. Differentiated cells can be isolated from a fetus or a live born animal, for example.

The term "undifferentiated cell" as used herein can refer to a precursor cell that has an unspecialized phenotype and is capable of differentiating. An example of an undifferentiated cell is a stem cell.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radioimmunoassay, or by colorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

"Selectable marker" as used herein refers to a molecule that when expressed in cells renders those cells resistant to a selection agent. Nucleic acids encoding selectable markers may also comprise such elements as promoters, enhancers, translational control sequences, poly A addition signals, transcriptional termination signals and the like. Suitable selection agents include antibiotic such as kanamycin, neomycin, and hygromycin.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim, an in the latter instance, impurities ordinarily associated with the specified material(s). The term "consisting essentially of" limits the scope of a claim to the specified elements, steps or materials and those that do not materially affect the basic and novel characteristic(s) of the claimed subject matter.

The following materials and methods are provided to facilitate the practice of the methods and compositions described in Example I.

Human PSC Culture and Differentiation

Human ESC lines H9 and CHB8 were obtained from the National Stem Cell Bank and Massachusetts Human Stem Cell Bank respectively. The human iPSC lines, iPSC 1 (CHOP_WT1.2) and iPSC 2 (CHOP_WT2.2) were derived from wild type human fibroblasts as described below. Human PSCs were maintained as described (Kennedy et al., 2007). For generating day 5 transient endoderm cells, human PSCs were differentiated in the serum free differentiation (SFD) media (Gadue et al., 2006) as either embryoid bodies (EBs) (Gouon-Evans et al., 2006) or monolayer cultures (D'Amour et al., 2006; Nostro et al., 2011). Further details are described below. One liter of SFD without growth factors contains the following components:

750 ml IMDM (homeade) powder-invitrogen, water-cellgro (Invitrogen: 12200-036, Cellgro cat #: 25-055-CM), 250 ml F12 (Cellgro cat #: 10-080-CV), 5 ml N2-SUPPLEMENT (Gibco cat #: 17502-048), 10 ml B27—retinoic acid (Gibco cat #: 12587-010), 5 ml 10% BSA (in PBS) (TC grade (low endotoxin) should test). SFD is stored in 150 ml bottles and supplements added as indicated on the day of differentiation.

For monolayer endoderm differentiation, PSCs were plated onto matrigel-coated dishes at 80% confluency. The cells were induced to differentiate by culturing in the RPMI-based serum free medium supplemented with 10% SFD, mouse Wnt3a (40 ng/ml) and Activin A (100 ng/ml) for one day. On the following two days the medium was switched to RPMI supplemented with BMP4 (0.5 ng/ml), bFGF (10 ng/ml), Activin A (100 ng/ml) and VEGF (10 ng/ml). Finally, during the following two days, the cells were differentiated in SFD supplemented with BMP4 (0.5 ng/ml), bFGF (10 ng/ml), Activin A (100 ng/ml) and VEGF (10 ng/ml). For hepatic differentiation of human ESCs, the cells were differentiated as monolayer cultures for 5 days to generate definitive endoderm as described above, and further differentiated for 4 weeks in the SFD-based hepatic induction medium supplemented with ascorbic acid (50 g/ml), monothioglycerol ($4.5 \times 10^{-4}$ M), BMP4 (50 ng/ml), bFGF (10 ng/ml), VEGF (10 ng/ml), EGF (10 ng/ml), TGF (20 ng/ml), HGF (100 ng/ml), Dexamethasone ($1 \times 10^{-7}$ M) and 1% DMSO. All cytokines were human and purchased from R&D Systems, unless stated otherwise. Human PSCs were maintained in a 5% $CO_2$ air environment, while all differentiation cultures were maintained in a 5% $CO_2$, 5% $O_2$, 90% $N_2$ environment.

Establishment and Maintenance of EP Cell Lines

EP cells were first purified from day 27 hepatocyte differentiation cultures of H9 ESCs by sorting for $CXCR4^+$/$CD117^{high}$ cells and culturing them in hepatic induction media on matrigel (BD Biosciences) with mouse fibroblast feeder (MEF) cells ($0.5 \times 10^6/58$ $cm^2$). The optimal culture conditions for maintaining EP cells was established by culturing cells on matrigel and MEFs as described above and eliminating cytokines that promote hepatocyte differentiation. This medium is composed of SFD-based media supplemented with BMP4 (50 ng/ml), bFGF (10 ng/ml), VEGF (10 ng/ml), and EGF (10 ng/ml) termed EP basic medium. EP cells from other PCS lines were established from day 5 transient endoderm by sorting for $CXCR4^+$/$CD117^{high}$ cells and maintaining them as described above in a 5% $CO_2$, 5% $O_2$, 90% $N_2$ environment. Cells were fed every two days, and were split at $1 \times 10^6/58$ $cm^2$ every 6 days by trypsinization. The small molecule inhibitors PD0325901 (Sebolt-Leopold et al., 2004; Ying et al., 2008), PD173074 (Mohammadi et al., 1998) and SB431542 (Laping et al, 2002; Inman et al., 2002) were purchased from Cayman Chemicals and Stemgent, respectively.

As mentioned above, SFD serum free medium consists of 75% IMDM (Invitrogen, 12200-036), 25% Ham's F12 (Cellgro), 0.5×N2-Supplement (Gibco), 0.5× B27 without retinoic acid (Gibco), 0.1% BSA (Sigma, A1470), 50 g/ml ascorbic acid phosphate magnesium (Wako), and $4.5 \times 10^{-4}$ M monothioglycerol. Matrigel-coated plates were prepared by plating 1.5 ml of undiluted growth factor reduced matrigel (BD Biosciences, 354230) per 58 $cm^2$ (100 mm) dish, and then allowed to solidify in a 37° C. incubator for 30 minutes. The two iPSC lines were generated from human dermal fibroblasts using the STEMCCA-loxp vector containing four reprogramming factors (OCT4, SOX2, KLF4, CMYC). iPSC lines with a single viral integrant were then transiently transfected with a CRE expression plasmid to obtain lines without the reprogramming factors as described previously (Somers et al., 2010). These cell lines display a typical iPSC phenotype (manuscript in preparation). The liver-derived EP cell line was established by sorting for $CXCR4+$/$CD117^{high}$ cells from day 24 hepatocyte differentiation cultures of H9 ESCs, and was maintained as described above.

Flow Cytometry and Cell Sorting

Single cell suspensions were obtained by dissociating day 5 transient endoderm, EP cell cultures, or EP cell differentiation cultures with 0.25% trypsin at 37° C. for 3-5 minutes. Cell surface antigen staining was performed in IMDM with 10% fetal calf serum. For intracellular staining, cells were fixed with 1.6% paraformaldehyde (Electron Microscopy Sciences) at 37 C for 20 minutes, and then washed twice with PBS+1% BSA. The fixed cells were permeabilized and stained in 1× Permeabilization Wash Buffer (BioLegend, 421002). The stained cells were analyzed with the BD FACS Canto II Flow Cytometer (BD Biosciences), and the data was analyzed using the Flowjo software (TreeStar). The sources and concentrations of primary, secondary antibodies and isotype controls are listed below.

Microarrays and Bioinformatics Analysis.

H9 ESCs (T0, ES), H9 ESC—derived DE (T5, DE) and EP cells (EPC) were purified by sorting for either $SSEA3^{high}$/$SSEA4^{high}$ undifferentiated cells or $CXCR4^{high}$/$CD117^{high}$ populations (for T5 DE and EPC). Approximately $1 \times 10^5$ cells were obtained for each sample. Three biological replicates of each cell type (ES, DE and EPC) were prepared, and total RNA was extracted using RNeasy Mini Kit (Qiagen). Quality-assessed RNA samples were hybridized to Affymetrix GeneChip HumanGene 1.0 ST arrays. Nine raw data files obtained by the Affymetrix scanner passed data quality control steps prior to RNA normalization through the Affymetrix expression console. The microarray data can be accessed at NCBI Gene Expression Omnibus, accession number GSE35461.

Endoderm Differentiation of EP Cells

For hepatic differentiation, EP cells were dissociated with 0.25% trypsin EDTA and then were re-plated onto matrigel (1:6 dilution) coated or gelatin coated 12-well tissue culture plates (BD) at $1 \times 10^5$ cells per well as adherent cultures. The hepatic differentiation medium for EP cells is SFD-based supplemented with ascorbic acid (50 g/ml), monothioglycerol ($4.5 \times 10^{-4}$ M), and various cytokines. During the first 6 days of differentiation, the following cytokines and growth factors were added: BMP4 (50 ng/ml), bFGF (10 ng/ml), VEGF (10 ng/ml), EGF (10 ng/ml), TGF (20 ng/ml), HGF (100 ng/ml) and Dexamethasone ($1 \times 10^{-7}$ M). In the next 6 days, bFGF (10 ng/ml), VEGF (10 ng/ml), EGF (20 ng/ml), HGF (100 ng/ml), OSM (20 ng/ml), Dexamethasone ($2 \times 10^{-7}$M), Vitamin K1 (6 g/ml), and γ-secretase inhibitor X (Calbiochem, 565771; 2 M) were added. Over the first 12 days of differentiation, 1% DMSO was added to the medium, but omitted in the final two weeks. From day 12 and afterwards, the media contained HGF (100 ng/ml), OSM (20 ng/ml), Dexamethasone ($2 \times 10^{-7}$ M), Vitamin K1 (6 g/ml), and 1% non-essential amino acids (NEAA) (Invitrogen). The medium was changed every 3 days. The drug inducibility assay was performed using P450-Glo™ CYP3A4 LuciferinIPA kit (Promega, V9002). Briefly, H9-EP cells (passage 15) were differentiated into hepatocytes for 24 days and then cultured in the presence (Rifampicin) or the absence (DMSO) of Rifampicin (Sigma; 25 μM) for 3 days, and compared to HepG2 cells. To confirm that the induced activity was specific for CYP3A4 enzyme, inhibition controls included the selective inhibitor ketoconazole (Sigma, 1 μM) in the presence of Rifampicin (25 μM). Net signal was calculated by subtracting background luminescence values (no-cell control) from Rifampicin or DMSO values.

For pancreatic differentiation of EP cells, a protocol described by Nostro et al. (2011), was modified by omitting the first step, and by adding-secretase inhibitor X (Calbiochem, 2 M) from day 8 to day 12 of differentiation, as well as by adding human insulin (Sigma, 800 pM) and nicotinamide (Sigma, 10 mM) from day 10 and onwards. To start differentiation, EP cells that had been expanded for 5 days in 100 mm tissue culture dishes were either cultured directly in the step 2 media or harvested and re-plated onto matrigel-coated (undiluted) 12-well dishes at $3 \sim 4 \times 10^5$ cells per well. Mouse Wnt3a was supplemented to the step 2 media at 3 ng/ml. From day 10 and onwards, the medium was alternated every day between high dextrose (60 mM) and low dextrose (20 mM). EP cells from passages 6 to 20 were used for pancreatic differentiations. Day 14-18 EP cell differentiation cultures were used for the c-peptide release assay. C-peptide release assays were performed as previously described (D'Amour et al., 2006), using Mercodia Ultrasensitive C-peptide ELISA kit (Mercodia). Briefly, after a 1-h wash in KRBH medium, 300 l of basal media that contains 2 mM D-glucose (Sigma) and 18 mM L-glucose (Alfa Aesar) were added to each well of 12-well dishes. After 1-h incubation, the basal media was removed, and 300 l of stimulation media (D-glucose 20 mM) were added. The cultures were incubated at 37 C in a 5% $CO_2$, 5% $O_2$, 90% $N_2$ environment for various time periods as indicated. For each experiment, 6 wells of supernatants were pooled together. About 30 human adult islets with a size average of 300 cells/islet were used for each assay. Insulin secretion was calculated based on the total cell number and the percentage of c-peptide+ cells of each experiment. The primary human islets were purchased from Prodo Laboratories Inc., and were maintained in Prodo islet medium (Standard)/PIM(S)™ supplemented with Prodo islet medium (Glu)/PIM(G)™ and Prodo islet medium (Human AB serum)/PIM(ABS)™. Human Islets were assayed for c-peptide release the second day after their arrival (4 days after islet processing).

For intestinal differentiation of EP cells, a modification of the protocol described by Spence et al. (2011) was used. Intact EP cell colonies were treated with BMP4 (500 ng/ml) and FGF4 (500 ng/ml) for 2 days, and were then harvested by digesting matrigel with collagenase B treatment at 37 C for 1 hour. The resultant colonies were mixed with undiluted matrigel (BD) supplemented with FGF4 (50 ng/ml) Wnt3a (100 ng/ml), R-spondin1 (500 ng/ml), EGF (50 ng/ml) and Noggin (100 ng/ml), and were re-plated onto 12-well dishes at $1.5 \sim 2 \times 10^6$ cells per well. SFD-based differentiation medium containing ascorbic acid phosphate magnesium (Wako, 50 g/ml), monothioglycerol ($4.5 \times 10$ M), FGF4 (50 ng/ml) Wnt3a (100 ng/ml), R-spondin1 (500 ng/ml), EGF (50 ng/ml) and Noggin (100 ng/ml) was used. FGF4 and Wnt3a were removed from the medium recipe from day 5 of differentiation, while BMP4 (20 ng/ml) was added at day 21 and onwards. Cells were fed every 2~3 days. Human colon tumor cell line CACO-2 was purchased from Sigma.

All of the differentiation cultures of EP cells were maintained in a 5% $CO_2$, 5% $O_2$, 90% $N_2$ environment. All cytokines were purchased from R&D. Dorsomorphin, KAAD cyclopamine and small molecule inhibitor SB431542 were purchased from Stemgent, and all-trans retinoic acid from Sigma.

Neuroectoderm and Mesoderm Differentiation of Human ES and EP Cells

To evaluate the potential of EP cells to differentiate into neuroectoderm or mesoderm, H9-EP cells (passage 5) and H9 ESCs were induced with conditions established for promoting hESC differentiation towards either neuroectoderm (Greber et al., 2011) or mesoderm. Undifferentiated H9 ES or EP cells were dissociated into small cell clumps and then replated onto matrigel-coated 12-well plates at $4.5 \times 10^5$ cells per well.

For neuroectoderm differentiation, the medium is composed of DMEM/F12, 1% N2 supplement (Gibco), 1% B27 supplement without retinoic acid (Gibco), β-mercaptoethanol (0.1 mM), 1% non-essential amino acids (Invitrogen), 1% L-Glutamine (Invitrogen), which is supplemented with inhibitors Noggin (250 ng/ml), SB431542 (15 μM) and PD0325901 (1 μM). Cells were harvested at days 4 and 8 by trypsinization.

For mesoderm differentiation, the medium for the first 3 days is RPMI-based, containing ascorbic acid (50 g/ml), monothioglycerol ($4.5 \times 10^{-4}$ M), and 1% L-Glutamine, and is supplemented with BMP4 (10 ng/ml), VEGF (50 ng/ml) and CHIR99021 (Cayman; 2 mM) for day 0 and day 1, and BMP4 (10 ng/ml), VEGF (50 ng/ml) and basic FGF (10 ng/ml) for day 2. The medium for days 3 and 4 mesoderm differentiation is StemPro 34-based (Invitrogen), containing ascorbic acid (50 g/ml), monothioglycerol ($4.5 \times 10^{-4}$ M), and 1% Glutamine, and is supplemented with BMP4 (10 ng/ml), VEGF (50 ng/ml) and basic FGF (10 ng/ml) for day 3, and VEGF (50 ng/ml) and basic FGF (10 ng/ml) for day 4. Cells were harvested at days 1 and 4 by trypsinization.

Immunohistochemistry

Samples were embedded in paraffin and sectioned at 6-10 um. Antigen retrieval by steaming slides in sodium citrate buffer for 30 min were performed for a subset of antigens as indicated in the Tables. Sections were blocked in the appropriate serum (5% serum in 1xDPBS+0.5% Triton-X) for 30 min. Primary antibodies were diluted in blocking buffer and incubated on sections for 3 hr or overnight at 4 C. Slides were washed and incubated in secondary antibodies in blocking buffer for 2-h at room temperature. For a list of antibodies and dilutions used, see Tables. The staining images were acquired using a Nikon Eclipse E800 fluorescence microscope with Phase 3 imaging software (Nikon).

Immunofluorescence

H9-EP cells were allowed to differentiate on matrigel-coated 12-well dishes for 18 days as described. Human islets were allowed to attach to matrigel-coated 12-well dishes.

Cells were fixed in wells with 4% PFA at 37 C for 10 minutes, and then washed twice in cold DPBS (with $CaCl_2$ and $MgCl_2$)+0.1% BSA (wash buffer), and permeabilized in wash buffer with 0.2% Triton-X100 for 20 minutes. After two washes, cells were blocked with 10% goat serum in DPBS (with $CaCl_2$ and $MgCl_2$)+2% BSA for 30 minutes at room temperature. Immunofluorescence was performed as described previously (Gouon-Evans et al., 2006) using the following antibodies: mouse anti-PDX1, rabbit anti-human C-peptide and mouse anti-Glucagon overnight at 4° C. Concentrations of isotype controls were matched to primary antibodies. Secondary antibodies used were: goat anti-rabbit IgG-Cy3, goat anti-mouse IgG1-Alexa 488 and goat anti-mouse IgG2b-Alexa 488. Cells were incubated with secondary antibodies for 1-h at room temperature. Primary and secondary antibodies were diluted in DPBS (with $CaCl_2$ and $MgCl_2$)+2% BSA+0.05% Triton-X100. Prolong Gold Antifade reagent with DAPI (Invitogen) was used to counterstain the nuclei. The stained cells were visualized using a fluorescence microscope (Leica DMI 4000B) and images captured using the Leica Application Suite software.

Teratoma/Transplantation Assay

EP cells ($8-10 \times 10^6$) were re-suspended in 300 nl of cold High Concentration Matrigel (BD Biosciences) which was supplemented with a combination of cytokines: BMP4 (50 ng/ml), bFGF (10 ng/ml), VEGF (10 ng/ml), and EGF (10 ng/ml) for gut-like endoderm differentiation in vivo, or FGF10 (400 ng/ml), VEGF (100 ng/ml), EGF (100 ng/ml) and BMPR1A (500 ng/ml) for hepatocyte differentiation in vivo. Cells were injected subcutaneously into the neck of SCID/Beige mice. Similarly, $1 \times 10^7$ cells from day 5 endoderm cultures of H9 ESCs, or 5×106 CXCR4+/CD117$^{high}$ cells sorted from day 5 endoderm cultures of H9 ESCs were injected and analyzed as described above. Also, $1 \times 10^7$ cells from day 20 hepatocyte differentiation cultures of H9 ESCs, or from day 9 hepatocyte differentiation cultures of H9-EP cells were injected with a cytokine combination of FGF 10 (200 ng/ml), VEGF (50 ng/ml), EGF (50 ng/ml), and HGF (200 ng/ml). Resultant matrigel plugs/transplants were analyzed as described.

Quantitative RT PCR

Total RNA was prepared with the RNAeasy Micro Kit (Qiagen) and treated with RNasefree DNase (Qiagen). RNA (500 ng to 1 ug) was reversely transcribed into cDNA using random hexamers and Oligo (dT) with Superscript III Reverse Transcriptase (Invitrogen). QPCR was performed on the LightCycler 480 II (Roche) using LightCycler 480 SYBR Green I Master Mix (Roche) as described previously (Nostro et al., 2008). Expression levels were normalized to the housekeeping gene PRIG (CYCLOPHILIN G). The oligonucleotide sequences are listed in the Tables. Total human intestine RNAs were purchased from Biochain.

Primary Antibody List

| Antibody | Target Species | Company | Product Code | Conjugates | Ig Species | Dilution |
| --- | --- | --- | --- | --- | --- | --- |
| Alpha Fetoprotein | Human | R&D Systems | MAB1368 | none | Mouse IgG1 | 1:400(IHC); 1:750 (Flow) |
| ASGPR1 (N18) | Human | Santa Cruz | sc-13467 | none | Goat | 1:200 (Flow) |
| CDX2 | Human | Biogenex | am3925m | none | Mouse IgG1 | 1:50 (IHC*); |
| CDX2 | Human | Abcam | ab76541 | none | Rabbit mAb | 1:40 (Flow) |
| CD26 | Human | Santa Cruz | sc-52469PE | PE | | 1:50 (Flow) |
| CD117/CKIT | Human | Caltag | CD11705 | APC | Mouse IgG | 1:100 (Flow) |
| CD117/CKIT | Human | Caltag | CD11704-4 | R-PE | Mouse IgG | 1:100 (Flow) |
| CD133 | Human | Invitrogen | CD11704-4 | PE Cy5.5 | Mouse IgG | 1:50 (Flow) |
| CD166/Alcam | Human | Santa Cruz | sc-53551PE | PE | Mouse IgG | 1:50 (Flow) |
| CD177/NB1 (MEM166) | Human | Abcam | ab77230 | APC | Mouse IgG | 1:50 (Flow) |
| CD184/CXCR4 | Human | Invitrogen | MHCXCR404 | PE | Mouse IgG | 1:100 (Flow) |
| CD184-/CXCR4 | Human | BD Pharmingen | 306504 | APC | Mouse IgG | 1:100 (Flow) |
| CD34 | Human | Caltag | CD34-581-05 | APC | Mouse IgG | 1:100 (Flow) |
| C-peptide | Human | Cell Signaling | 4593 | none | Rabbit | 1:30 (Flow) |
| Foxa1/HNF3a | Human | Santa Cruz | sc-101058 | none | Mouse IgG2a | 1:100 (Flow) |
| FoxA2 (363-457) | Human | Abnova | H00003170-M12 | none | Mouse IgG1 | 1:500 (IHC*) |
| Glucagon (K79bB10) | Human | Sigma | G2654 | none | Mouse IgG1 | 1:1000 (Flow) |
| HFN4-alpha (C11F12) | Human | Cell Signaling | 3113S | none | Rabbit mAb | 1:50 (IHC*) |
| Human Nuclei | Human | Millipore | MAB1281 | none | Mouse IgG | 1:50 (IHC) |
| Intestinal FABP | Human | Abcam | ab60272 | none | Goat | 1:500(IHC) |
| LGR5 | Human | Abgent | AP2745d | none | Rabbit | 1:20 (Flow) |
| Mucin2 (B306.1) | Human | Santa Cruz | sc-59859 | none | Mouse IgG1 | 1:200 (IHC) |
| N-Cadherin | Human | Sigma | C3865 | none | Mouse IgG1 | 1:200 (Flow) |
| PDX-1 | Human | R&D | MAB2419 | none | Mouse IgG2b | 1:150 (0.2 mg/ml stock)(Flow) |
| Somatostatin (H11) | Human | Santa Cruz | sc-74556 | none | Mouse IgG1 | 1:50 (Flow) |
| Sox17-Biotin | Human | R&D | AF1924 | Biotin | Goat | 1:50 (0.1 mg/ml Stock)(Flow) |
| SSEA-3 Alexa Flour 647 | Human | Biolegend | 330306 | Alexa Fluor 488 | Rat | 1:400 (Flow) |
| SSEA-4 PE | Human | BioLegend | 330408 | Alexa Fluor 647 | Mouse | 1:100 (Flow) |
| Synatophysin | Human | Sigma | S5768 | none | Mouse IgG1 | 1:100 (Flow) |
| TTF1/NKX2-1 (EP1584Y) | Human | Novus Biologicals | NB100-80062 | none | Rabbit mAb | 1:30 (Flow) |
| Villin(V20) | Human | Santa Cruz | sc-33347 | none | Goat | 1:500 (IHC) |

*Antigen Retrieval

IgG Controls

| IgG control | Company | Product Code | Concentration |
| --- | --- | --- | --- |
| Goat IgG | Santa Cruz | sc-2028 | 0.4 mg/ml stock |
| Goat IgG, biotinylated | R&D | BAF108 | 0.1 mg/ml stock |
| Rabbit IgG | Cell Sinaling | 39005 | 2.5 mg/ml stock |
| GST/mouse IgG1 (1C9) | Santa Cruz | sc-80004 | 0.2 mg/ml |
| Mouse IgG2a | Santa Cruz | sc-3878 | 0.2 mg/ml |
| Mouse IgG2b | Santa Cruz | sc-3879 | 0.2 mg/ml stock |

| Gene | Sequence | Product Length |
| --- | --- | --- |
| AAT | Forward 5'- AGGGCCTGAAGCTAGTGGATAAGT -3'<br>Reverse 5'- TCTGTTTCTTGGCCTCTTCGGTGT -3' | 132 |
| AFF | Forward 5'- CTACCTGCCTTTCTGGAAGAACTTTG -3'<br>Reverse 5'- TCTGTTTCTTGGCCTCTTCGGTGT -3' | 156 |
| ALB | Forward 5'- GTGAAACACAAGCCCAAGGCAACA -3<br>Reverse 5'- TCCTCGGCAAAGCAGGTCTC -3' | 150 |
| ASGR1 | Forward 5'- AGGACTGTGCCCACTTCACC -3'<br>Reverse 5'- TGGCCTTGTCCAGCTCTGTCT -3' | 113 |
| CDX2 | Forward 5'- TCCTGGTCTGGGAAGGGAAGAGAAA -3'<br>Reverse 5'- CGGAAGCCAAAGGCAGCTAAGATAG -3' | 159 |
| CYCLOPHILIN | Forward 5'- GAAGAGTGCGATCAAGAACCCATGAC -3'<br>Reverse 5'- GTCTCTCCTCCTTCTCCTCCTATCTTT -3' | 163 |
| CYP3A4 | Forward 5'- GTGACCAAATCAGTGTGAGGAGGTA -3'<br>Reverse 5'- AGGAGGAGTTAATGGTGCTAACTGG -3' | 98 |
| CYP3A7 | Forward 5'- ACCCTTTGGAAGTGGACCCAGAAA -3'<br>Reverse 5'- AGAAGTTCTGAAGGACTCTGACTAGA -3' | 102 |
| FOXF1 | Forward 5'- CCCGTCCAAGGCCAAGAAGA -3'<br>Reverse 5'- TGACGATGAGCGCGATGTAGGAATAG -3' | 161 |
| G6PC | Forward 5'- TACCGCACTCTTGCAGAAGGACAA -3'<br>Reverse 5'- TGCACGTCTTTGACTCCTTGAAACCC -3' | 112 |
| GLUCAGON | Forward 5'- TTCCCAGAAGAGGTCGCCATTGTT -3'<br>Reverse 5'- CAACCAGTTTATAAAGTCCCTGGCGG -3' | 103 |
| HNF4A | Forward 5'- TCCAACCCAACCTCATCCTCCTTCT -3'<br>Reverse 5'- TCCTCTCCACTCCAAGTTCCTGTT -3' | 136 |
| INSULIN | Forward 5'- TTTGTGAACCAACACCTGTGCGG -3'<br>Reverse 5'- GCGGGTCTTGGGTGTGTAGAAGAA -3' | 157 |
| KLF5 | Forward 5'- TATCTGACACCTCAGCTTCCTCCAGT -3'<br>Reverse 5'- TGTTACGCACGGTCTCTGGGATTT -3' | 106 |
| LGR5 | Forward 5'- TTTGGACAAGGGAGACCTGGAGAA -3'<br>Reverse 5'- AGAGGAGAAGGACAAGAAAGCCACA -3' | 98 |
| LYSOZYME | Forward 5'- GGCCAAATGGGAGAGTGGTTACA -3'<br>Reverse 5'- TTGCCATCATTACACCAGTAGCGG -3' | 136 |
| MAFA | Forward 5'- TGCAGCAGCGGCACATTC -3<br>Reverse 5'- CGCCAGCTTCTCGTATTTCTCCTTGT -3' | 89 |
| MAFB | Forward 5'- CTGCTCAAGTTCGACGTGAAGAAGGA -3'<br>Reverse 5'- TAGTTGCTCGCCATCCAGTACAGA -3' | 162 |
| MUCIN2 | Forward 5'- TGCAGTGTGATGTCTCTGTTGGGT -3'<br>Reverse 5'- ATCCATGGGCCAGCAACAATTGAC -3' | 108 |
| NEUROD | Forward 5'- CCCATGGTGGGTTGTCATATATTCA -3'<br>Reverse 5'- CCAGCATCACATCTCAAACAGCAC -3' | 143 |
| NGN3 | Forward 5'- TCACTCAAGTCTGTCTGCCTCTCA -3'<br>Reverse 5'- AAATCCCGGACCTGATTGGGAGTA -3' | 152 |
| NKX2.1 | Forward 5'- GCATGAACATGAGCGGCATGG -3'<br>Reverse 5'- GCCGACAGGTACTTCTGTTGCTT-3' | 112 |
| NKX6.1 | Forward 5'- AGGACGACGACTACAATAAGCCTCTG -3'<br>Reverse 5'- CGCTGCTGGACTTGTGCTTCT -3' | 126 |
| PDX1 | Forward 5'- CTCCACCTTGGGACCTGTTTAGAGA -3'<br>Reverse 5'- CGCCCGAGTAAGAATGGCTTTATGG -3' | 135 |
| SOMATOSTATIN | Forward 5'- GAGAATGATGCCCTGGAACCTGAAGA -3'<br>Reverse 5'- ATTCTTGCAGCCAGCTTTGCGT -3' | 125 |
| VIL1 | Forward 5'- AGCTCCTCTACAGGCTTGTTCACT -3'<br>Reverse 5'- GGACGTGTTCAATGCTAACAGCAACC -3' | 139 |

The following examples are provided to illustrate certain embodiments of the invention. They are not intended to limit the invention in any way.

EXAMPLE I

To address the drawbacks of current protocols, we generated self-renewing DE progenitor lines from both human ESCs and iPSCs. These cells, termed EP cells for endodermal progenitor cells, display a proliferative capacity similar to ESCs yet lack teratoma-forming ability. In addition, EP cell lines generate endodermal tissues representing liver, pancreas, and intestine, both in vitro and in vivo. Thus, EP cell lines provide a powerful reagent to study how different gut tissues are specified from a common multipotent endodermal progenitor and to optimize mono-lineage differentiation. Moreover, creation of EP cells from ESCs/iPSCs may represent a strategy to optimize the production of pure, non-tumorigenic cells for tissue replacement therapies.

Identification of a Definitive Endoderm Progenitor Population from Human PSCs

We adapted a step-wise differentiation protocol in serum free media that was previously shown to induce DE and its derivative hepatic lineages from mouse and human ESCs (Gadue et al., 2006; Gouon-Evans et al., 2006). This protocol uses Activin A to induce DE and then BMP4 and bFGF amongst other factors to specify a hepatic fate from DE, in a process that mimics embryogenesis. Using a variation of this protocol (see Experimental Procedures) we could generate hepatic cells after two weeks of induction (data not shown). Interestingly, after 3-4 weeks, these cultures contained two cell populations with distinct morphology (FIG. 1A). One population resembled immature hepatocytes, being large and highly vacuolated (FIG. 1A, "Differentiated Cells"), while the other population resembled undifferentiated ESC colonies (FIG. 1A, "Progenitor Colonies"). These mixed cultures maintained both colony types after passaging for over nine months (data not shown). We used a pipette to manually isolate colonies of a given morphology and performed gene expression analysis using QRT-PCR (FIG. 1B). The ESC markers NANOG and OCT4 were not expressed in either cell type suggesting that these colonies were not an outgrowth of contaminating ESCs in the culture. The early hepatocyte marker AFP was enriched in the differentiated colonies while the early pan-endoderm marker SOX17 was enriched in the putative progenitor colonies. The early endoderm/liver/pancreas marker HNF4A (Duncan et al., 1997) was found in both. Based on these findings, we hypothesized that the undifferentiated colonies might represent endoderm progenitor (EP) cells undergoing both self-renewal and differentiation into hepatocytes in culture.

The bulk differentiation cultures were then examined by flow cytometry for expression of KIT (CD 117) and CXCR4, which are expressed on early endoderm (Gouon-Evans et al., 2006; D'Amour et al., 2005). A subpopulation of CXCR4+ CD117+ cells (3%-60%) was consistently present in the cultures (FIG. 1C and data not shown). These double-positive cells also express the pan-endoderm marker FOXA1 (Ang et al., 1993) and SOX17, which is expressed transiently in immature endoderm in vivo (Kanai-Azuma et al., 2002). The CXCR4+CD117+FOXA1+SOX17+ population likely marks putative EP cells from the undifferentiated colonies, which we showed to be enriched for SOX17 mRNA (FIG. 1B). To test this, we used FACS to isolate CXCR4+ and CXCR4− cells for further study. The early hepatocyte marker AFP was enriched in the CXCR4− cells while the CXCR4+ population expressed the immature endoderm marker SOX17 and was negative for AFP expression (FIG. 2A). Purified CXCR4+ cells could be expanded in culture but within three passages, reverted to a mixed population containing both SOX17+ and SOX17− cells, indicative of differentiation in culture (FIG. 2A, right panel). In contrast, the CXCR4− population had little proliferative capacity, consistent with a more mature phenotype of differentiated hepatocytes in vitro (data not shown).

Our data indicate that self-renewing EP cells can be produced through in vitro manipulation of human ESCs. Differentiation of CXCR4+ EP cells into AFP-expressing hepatocytes was expected in our initial experiments (FIG. 1), as the culture conditions were initially formulated to drive hepatocyte differentiation (Gouon-Evans et al., 2006). To better expand the EP cell population while maintaining the FOXA1+SOX17+ phenotype of these cells, we identified culture conditions, which consist of a serum free media containing BMP4, basic FGF (bFGF), EGF and VEGF plated on matrigel and MEF feeders (see Methods). Utilizing Matrigel was critical as suspension cultures were unable to maintain EP cells (data not shown).

Using these optimized culture conditions, we developed a simplified protocol for EP cell production. Human ESCs or iPSCs were induced to differentiate in the presence of high Activin A, which promotes endoderm formation (D'Amour et al., 2005). Definitive endoderm cells (CXCR4+CD 117+) were purified by cell sorting and cultured directly in EP cell medium (FIG. 2B, left panel). When cultured in the optimized conditions, the majority of cells form epithelial structures reminiscent of gut epithelium and contain what appears to be a central lumen, especially at higher cell density (FIG. 2B, right panel). Both ESC derived and iPSC derived EP cell lines proliferated extensively and displayed a homogenous EP cell phenotype (FOXA1+SOX17+FOXA2+)(FIG. 2C and data not shown). The optimized culture conditions could also maintain EP lines generated from 3-4 week liver differentiation cultures as described in FIG. 1 (liver-derived EP cell). These cells displayed similar characteristics as EP cells derived directly from definitive endoderm (data not shown).

We were able to derive EP cell lines from the human ESC lines H9 and CHB8 and from two human iPSC lines (H9-EP, CHB8-EP, iPS1-EP and iPS2-EP; see Methods). Endoderm progenitor populations generated from all of these PSC lines have been maintained for more than 20 passages with an expansion of $>10^{16}$ while maintaining the progenitor phenotype (FIG. 2C and data not shown). Thus, self-renewing EP lines can be generated reproducibly from human PSCs. Expansion of EP cells is not associated with a "crisis" where cells undergo a high rate of senescence as indicated by a transient flattening of the growth curve (FIG. 2C). Moreover, karyotype analyses were performed on EP cells derived from H9 ESCs and one iPSC line and were found to be normal (FIG. 3). These data indicate that the high rate of EP proliferation is not due to acquired genetic instability or chromosomal rearrangements. Cryopreserved EP cells can be thawed with high viability (data not shown). Among the cytokines used, BMP4 and FGF signaling were the most critical for EP cell maintenance. Withdrawal of BMP4 led to an almost complete loss of SOX17 expression within one week, and up-regulation of PDX1 indicating pancreatic differentiation (FIG. 4A). Withdrawal of bFGF or disruption of the FGF/Ras/MEK pathway with the small molecule inhibitors PD173074 and PD0325901 reduced proliferation dramatically (FIG. 4B), consistent with previous reports that FGF signaling is essential for DE expansion (Morrison et al., 2008). Withdrawal of VEGF or EGF also led to a significant decrease in proliferation (FIG. 4B). TGF-β signaling was also found to be essential for maintaining the EP cells as treatment with a small molecule inhibitor of TGF-β signaling, SB431542, completely abolished SOX17 expression in these cells and drastically suppressed proliferation (FIGS. 4C and 4D). The inhibition of TGF-β signaling in EP cells also inhibited differentiation into pancreatic β-cells, possibly due to spontaneous differentiation prior to pancreatic induction (FIG. 4E).

Nine sub-clones from the H9-EP cell line were established by depositing single CXCR4+CD117+ cells into 96-well plates to expand. These clones displayed the same proliferative capacity and marker expression as the parental line (data not shown). Thus, we have established clonal populations of EP cell lines that exhibit extensive proliferative capacity and express markers of early multipotent endoderm.

Characterization of EP Cells

We used gene expression microarrays to compare the transcriptomes of purified H9 ESCs, Activin A-induced day 5 transient endoderm, and H9-EP cells (FIG. 2A) (see Methods). Cluster analysis of the microarray data revealed that EP cells are more similar to day 5 transient endoderm than ESCs (FIG. 5A). Principal component analysis revealed that while EP cells are more similar to transient endoderm than ESCs, they are also distinct from transient endoderm (FIG. 5B). As expected, high level expression of the pluripotency markers NANOG, OCT4, SOX2, and DNMT3B was limited to ESCs (FIGS. 5C and 5D). Interestingly, the proto-oncogene MYCN was expressed in both ESCs and EP cells. MYCN is required for pluripotency and self-renewal of mouse ESCs (Varlakhanova et al., 2010) and may have a similar role in EP cells. Genes expressed in the primitive streak or mesendoderm, including CER1, FGF17, FGF8, GSC, and MIXL1 are expressed in day 5 transient endoderm but not EP cells, while a subset of genes including EOMES and LHX1 are maintained in both cell types (FIGS. 5C and 5D). As expected, expression of most endodermal genes including FOXA2, FOXA3, GATA4, and SOX17 was limited to day 5 endoderm and EP cells (FIGS. 5C and 5D).

Figure 1:
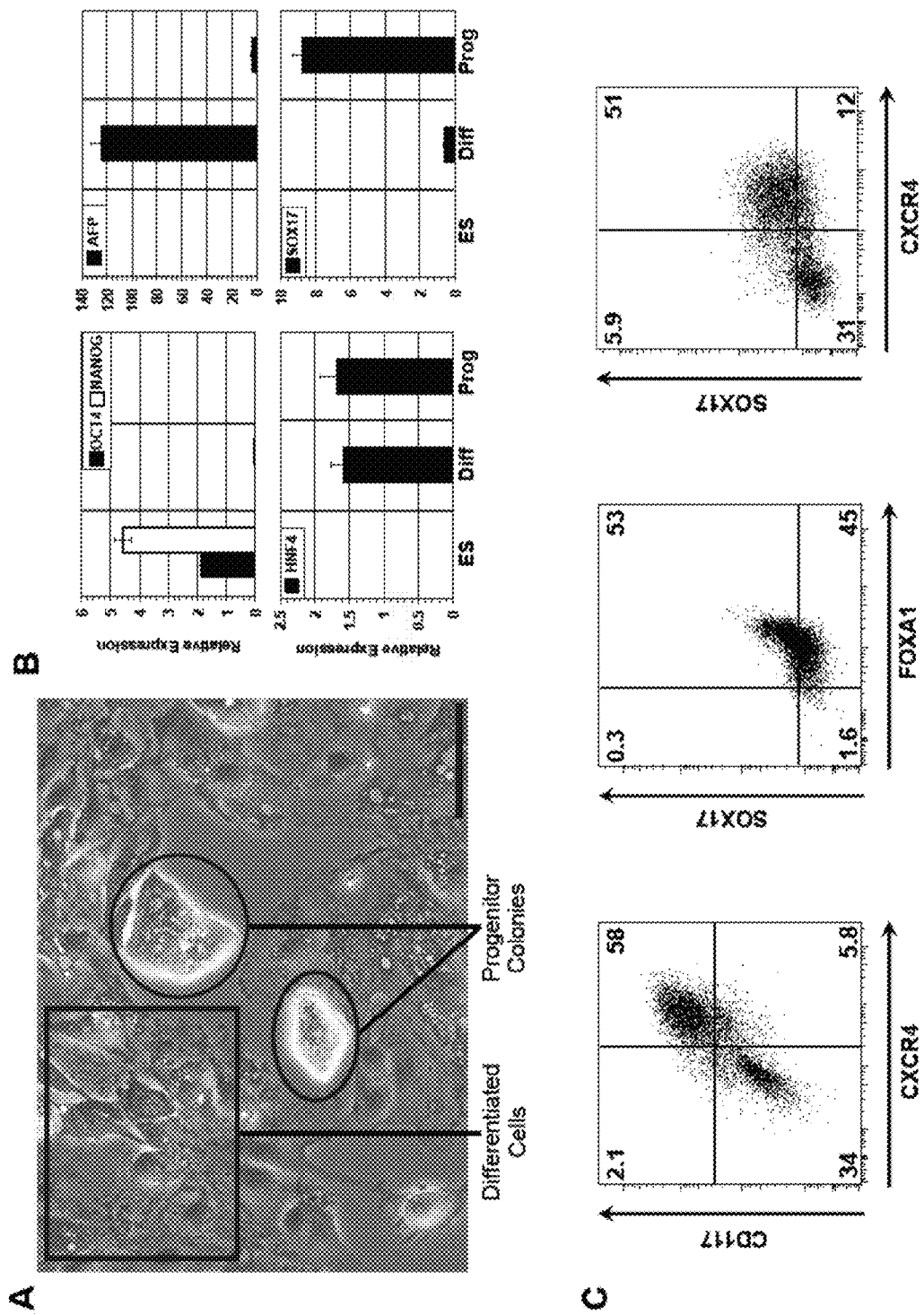
FIG. 1. A Putative Definitive Endoderm Progenitor Population is Identified in Differentiation Cultures from Human ESCs. The human ESC line H9 was differentiated towards the hepatic lineage. (A) Phase contrast image of a culture maintained for 4 weeks shows two distinct types of populations (Differentiated vs. Progenitor). The scale bar represents 100 um. Image was captured with 20× objective. (B) Colony types indicated in A were manually picked and pooled into groups, and gene expression was analyzed by quantitative real-time RT-PCR, comparing to undifferentiated ESCs. (Abbreviations—ES: embryonic stem cells; Diff: differentiated cells; Prog: progenitor colonies) The expression of indicated genes is shown normalized to the housekeeping gene CYCLOPHILIN. Values represent the mean of three individual pools of each population. Error bars represent the standard errors. (C) Cultures were assayed for CD117 (KIT) versus CXCR4, SOX17 versus FOXA1, and SOX17 versus CXCR4 by flow cytometry in three separate stains.
Figure 2:
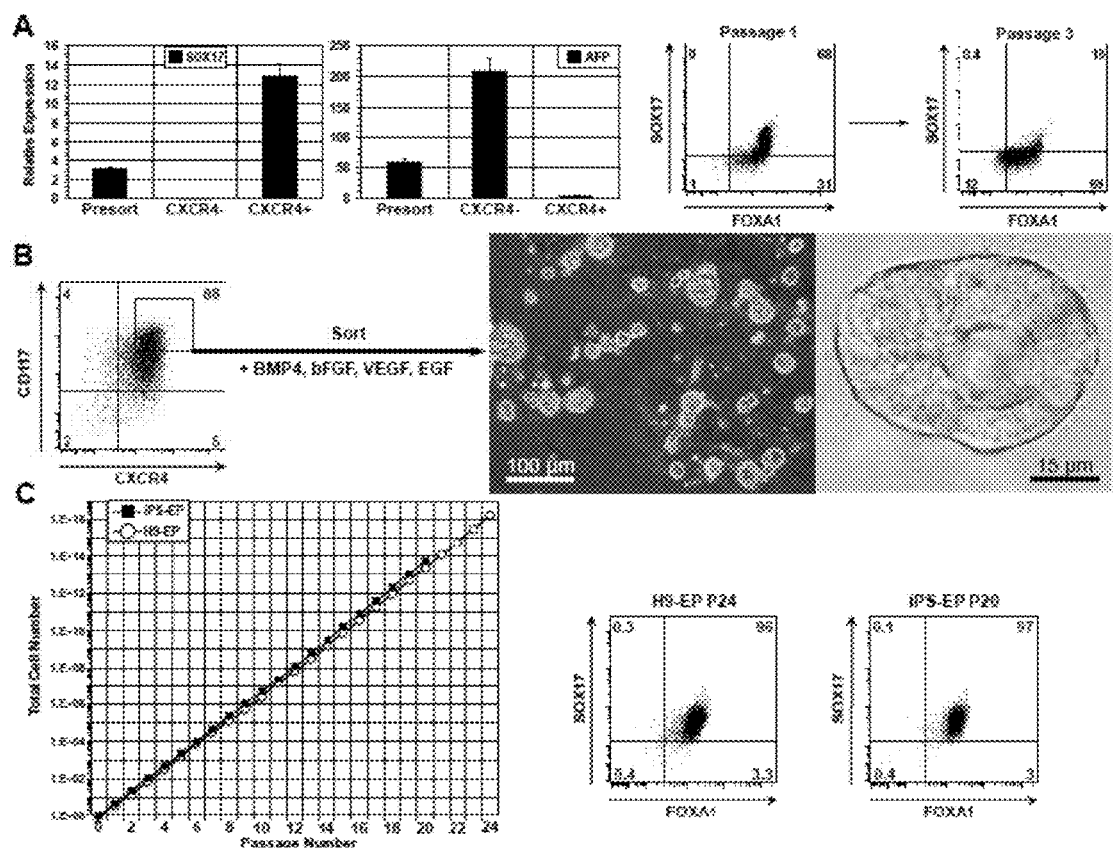
FIG. 2. Purification and Maintenance of Endodermal Progenitor Cells. (A) Cultures containing endoderm progenitors as in FIG. 1 were sorted based upon CXCR4 expression. Gene expression was analyzed by QRT-PCR. CXCR4+ cells were cultured as in FIG. 1 and after 1 or 3 passages, cultures were assayed for SOX17 versus FOXA1 expression by intracellular flow cytometry. (B) EP cell lines are established by sorting definitive endoderm (CXCR4+ CD117high) cells from day 5 of human ESC differentiation cultures induced with high levels of Activin A, and culturing the cells in optimized conditions (see text). Images show typical morphology of EP cell colonies (H9-EP), captured using 10× and 20× objectives. (C) EP cell lines derived from H9 ESCs or iPSCs were cultured and cell growth analyzed by cell count at each passage. Left panel: graph shows relative cell growth over time (Square: iPSC2 derived EP cell line; Circle: H9 derived EP cell line). Right panel: SOX17 versus FOXA1 expression by intracellular flow cytometry after either 24 (H9-EP) or 20 passages (iPSC2-EP).

The microarray data predicted surface markers that may be used to distinguish EP cells from ESCs and day 5 transient endoderm (FIG. 5C). For example, the ESC marker CD9 was depleted in EP cells. Messenger RNAs encoding endodermal markers CXCR4 and CD117 were expressed in both EP cells and transient endoderm (FIG. 5C), confirming our flow cytometry studies (FIGS. 1 and 2). In contrast, activated leukocyte adhesion molecule ALCAM/CD166 (Bowen et al., 1995) was expressed only by EP cells but not day 5 transient endoderm, while CD177/NB1, a glycoprotein expressed by neutrophils (Stroncek et al., 2007), was reduced in EP cells compared to day 5 endoderm (FIG. 5C). The stem cell/progenitor markers CD133, CD34 and LGR5 (Mizrak et al., 2008; Barker et al., 2010) were also expressed at relatively high levels in EP cells. Differential expression of a subset of the cell surface markers predicted by the microarray studies was confirmed by flow cytometry on ESCs, EP cells and day 5 endoderm, demonstrating that ALCAM and LGR5 are enriched on EP cells (FIG. 5E).

Our data indicate that EP cells closely resemble nascent endoderm, yet exhibit key differences in gene expression. The microarray data were analyzed for transcriptional regulators that are enriched in EP cells and therefore, might confer unique biological properties to this population. The top 13 hits are shown in Table 1, along with the fold increase in expression over day 5 transient endoderm. GATA3, a GATA family member enriched in mouse DE (Sherwood et al., 2007) ranks first in the list. HEY2, a target of Notch signaling, is enriched in EP cells, suggesting a possible role of Notch signaling in EP cell maintenance. Interestingly, transcription factors known to be important regulators of early liver (TBX3) (Ludtke et al., 2009), pancreas (ISL1 and RFX6) (Ahlgren et al., 1997; Smith et al., 2010), lung (FOXP2) (Shu et al., 2001), and intestine (ISX1) (Choi et al., 2006) were enriched in EP cells, suggesting the capacity to form these multiple endodermal lineages.

TABLE 1

Transcriptional Regulators Enriched in EP Cells. Gene expression was analyzed by microarray as described in FIG. 5. The top 13 transcriptional regulators that were enriched in EP cells over transient definitive endoderm are shown.

| Gene | Fold Expression (EP cell/transient endoderm) |
| --- | --- |
| GATA3 | >10x |
| TBX3 | 7.8x |
| ID2 | 8.4x |
| MSX2 | 8.2x |
| RFX6 | 8x |
| MEIS2 | 6x |
| ID1 | 5.5x |
| SALL1 | 4.3x |
| HEY2 | 3.4x |
| FOXP2 | 3.4x |
| ISL1 | 3.1x |
| LMO7 | 3.0x |
| ISX | 2.7x |

EP Cells Exhibit Multi-Lineage Endodermal Differentiation In Vitro

We next tested whether expanded EP cells retain the ability for multipotent endodermal differentiation upon manipulation of culture conditions. EP cell lines were differentiated under conditions known to promote hepatocyte, pancreatic or intestinal specification in vitro (Gouon-Evans et al., 2006; Nostro et al., 2011; Spence et al., 2011). For all induction protocols, EP cells were assumed to be at the DE stage and were stimulated as such. Representative data are shown for a polyclonal H9-EP cell line and two single cell derived sub-clones (FIGS. 6, 7, 8, 9, and 10). In addition, hepatocyte and pancreatic differentiation from two iPSC-derived EP cell lines (iPS1-EP and iPS2-EP) were examined with similar results (FIGS. 8 and 9).

To induce hepatocyte specification, EP cells were stimulated using a step-wise protocol adapted from previously published studies (see Methods)(Gouon-Evans et al., 2006; Basma et al., 2009). Hepatocyte differentiation was monitored at days 14, 20, and 27 of induction by QRT-PCR and by flow cytometry at day 20. By day 20 most cells exhibited features of hepatocyte morphology including polygonal shape and multi-nuclearity (FIG. 8A). QRT-PCR analysis revealed up-regulation of the hepatic markers alpha-1-antitrypsin (AAT), alpha-fetoprotein (AFP), Albumin (ALB), CYP3A4, CYP3A7 and Glucose-6-phosphatase (G6PC) (FIGS. 6A and 8B). Intracellular flow cytometry at day 20 of differentiation showed that more than 90% of cells were AFP+ and more than 80% of cells expressed AAT, indicating commitment to the hepatocyte fate (FIGS. 6B and 8C). The mature hepatocyte marker ASGPR1 (Basma et al. 2009) was expressed on about 20% of the cells while the EP cell marker CXCR4 was absent (FIG. 6B). EP cells generated from two iPSC lines also differentiated into hepatocytes (FIG. 8B). When treated with Rifampicin, EP cell-derived hepatocytes exhibited inducible CYP3A4 activities comparable to HepG2 cells (FIGS. 6C and 8D). Thus, EP cells consistently exhibit hepatocyte potential.

Endoderm components of liver and pancreas are thought to arise from the putative common foregut precursor (Spence et al., 2009). To investigate the pancreatic potential of EP cells, we modified the protocol reported by Nostro et al. (2011)(see Methods) Immuno-fluorescence analysis of differentiated EP cultures showed colonies that contain c-peptide+ but no Glucagon+ (GCG+) cells as compared to primary human islets that express both of these hormones (FIG. 7A). Colonies generated from EP cells were also PDX1+, indicative of pancreatic specification (FIG. 7A). PDX1 expression was confirmed by flow cytometric analyses at days 10-11 of differentiation both in the H9-EP cell line (not shown), single cell derived sub-clones, and two iPSC derived EP cell lines (FIG. 9A). In addition, approximately 5-30% of the differentiated EP cells (H9 and iPSC derived) expressed c-peptide by day 14 of pancreatic induction (FIGS. 7B and 9A). The efficiency of c-peptide+ cell generation was variable depending on the genetic background of the cell line (FIGS. 7B and 9A). However, c-peptide+ cells generated from all EP cell lines, regardless of genetic background, were negative/low for GCG and Somatostatin (SST) expression (FIGS. 7A, 7B, and 9A). We also examined the differentiation cultures by QRT-PCR. Consistent with pancreatic differentiation, expression of PDX1, NKX6-1 and NEUROD1 were strongly induced (FIGS. 7C and 9C), while the expression of the EP cell marker SOX17 declined (FIG. 9C). Transient expression of NEUROG3 (NGN3) in the EP cell differentiation cultures is indicative of endocrine specification (FIG. 9C). Insulin (INS) RNA was robustly induced with levels approximately 20% of that found in adult islets. When these data are corrected for the percentages of c-peptide+ cells in the samples (islet ~60%, H9-EP 15±3%, H9-EP clone 2 22±4%) (FIG. 7C), the levels of INS RNA in EP derived β-cells are estimated to be ~70% of that found in primary β-cells. This is consistent with protein levels of c-peptide comparing primary β-cells and EP derived pancreatic cells as determined by intracellular flow cytometry (FIG. 7E). Notably, MAFA, a critical transcription factor expressed in mature β-cells was upregulated in the EP cell differentiation cultures (FIG. 7C) to 30% the level of RNA found in adult islets. If the same correction for INS expression is used then both MAFA and NKX6-1 may be expressed in EP derived c-peptide+ cells at comparable levels to adult β-cells.

Importantly, c-peptide+ cells derived from EP cells exhibit minimal expression of GCG and relatively low expression of SST (FIGS. 7B and 7C). This contrasts with the majority of reports describing the generation of c-peptide+ cells from human PSCs, in which most pancreatic endocrine progeny display a polyhormonal phenotype (D'Amour et al., 2006; Nostro et al, 2011; Rezania et al., 2011). Polyhormonal pancreatic cells are found during mouse development but do not contribute to the β-cell population in the adult mouse (Herrera, 2000). In agreement, H9 ESCs exposed to the same pancreatic differentiation protocol produced a greater proportion of poly-hormonal cells compared to pancreatic endocrine cells derived from EP cells (FIG. 7D). EP cells generated a c-peptide+ population with less than 2% of the cells co-expressing GCG and ~5% of the cells co-expressing SST. In contrast, c-peptide+ cells generated directly from ESCs were 38±9% GCG+ and >20±1% SST+ (FIG. 7D). Thus, c-peptide+ cells generated from multiple EP cell lines are more similar to mature β-cells than populations generated directly from PSCs.

Previous reports have shown that poly-hormonal cells derived from ESCs are not fully functional and cannot efficiently respond to glucose stimulation by releasing insulin (D'Amour et al., 2006). A time course analysis of glucose induced c-peptide release was performed, comparing EP cell (H9-EP and iPS2-EP)-derived pancreatic differentiation cultures to primary human islets (FIGS. 7F and 9D). Data were collected over 40 minutes of stimulation with 20 mM glucose and was normalized, setting the 5-minute basal stimulation time point for each culture as 1. The kinetics of c-peptide release was similar between the EP derived cultures and primary human islets, with a consistent 3-fold stimulation index in the high glucose group over basal (low glucose) conditions. EP derived cultures were statistically indistinguishable from primary islets, with the exception of the 10 minute time point. When the cells were challenged again after 3 or 18 hours, they remained responsive to glucose stimulation in a similar manner as the first challenge (data not shown), indicating that these cells maintain glucose responsive-function. Assuming all of the proinsulin is processed into c-peptide and insulin at a 1:1 molar ratio, the c-peptide release assay revealed an estimated secretion of 9±1.7 ng insulin per $10^5$ EP cell-derived c-peptide+ cells (n=3), which is ~20% of the secretion of adult islet β-cells (estimated at 37 ng/$10^5$ cells, n=2; and Lukowiak et al., 2001). These findings demonstrate that EP cell-derived β-cells are functionally responsive to the physiologic stimulus (D-glucose) for insulin release in a manner similar to that of adult islets in vitro.

To compare the differentiation capacities of the EP cells derived from day 5 transient endoderm and the EP cells derived from liver differentiation cultures of ESCs, liver-derived EP cells were allowed to differentiate in the aforementioned liver or pancreas conditions. These cells generated hepatocyte progenitors that expressed AFP and AAT (FIG. 8C) and pancreatic cells that expressed PDX1 and c-peptide but not glucagon (FIG. 9A, bottom panel), with efficiencies similar to the EP cells derived from transient endoderm. These data suggest that EP cells are a robust stem cell population that can be generated from multiple stages of differentiation while maintaining multi-potency.

Liver and pancreas are of foregut origin. We next determined whether EP cells could produce intestinal epithelia, which arises from mid/hindgut regions. Using a protocol similar to that of Spence et al. (2011), we induced EP cells to undergo intestinal differentiation (see Methods). Typical "organoids" indicative of intestinal differentiation were identified upon day 30 of induction (FIG. 10A). These cultures expressed CDX2 and KLF5, transcription factors enriched in mid-hindgut lineages (Spence et al., 2011), and the Paneth cell marker Lysozyme (LYZ) (FIG. S6B). In contrast, the intestinal stem cell marker LGR5, which is also expressed on EP cells, was down-regulated after 30 days of induction to levels similar to adult intestine. Intracellular flow cytometric analysis revealed that 85-90% of cells expressed CDX2 at day 30 of differentiation, similar to the intestinal tumor cell line CACO-2 (FIG. 10C). These data indicate that EP cells have intestinal potential.

To determine if EP cell developmental potential was restricted to endodermal lineages, cultures were induced with conditions established to drive ESCs towards either neuroectoderm (Greber et al, 2011) or mesoderm. The upregulation of neuroectoderm markers ZIC1, SOX1, or PAX4 (FIG. 11A), and mesoderm markers MIXL1, T, or PECAM (FIG. 11B), were not observed suggesting that EP cells are committed to the endoderm germ layer.

EP Cells Lack Tumorigenicity and Form Endodermal Tissues In Vivo

The propensity for ESCs and iPSCs to form teratomas represents a major impediment to transplantation studies. To determine if EP cells retain tumor forming potential, 0.5 million H9 ESCs or H9-EP cells were transplanted intramuscularly into immune compromised mice. After 4-6 weeks, all mice injected with H9 ESCs developed tumors while mice injected with an equal number of EP cells did not (FIG. 12A). In fact, it was difficult to detect any injected EP cells under these conditions. Therefore, larger numbers ($8\text{-}10\times10^6$) of EP cells were transplanted in concentrated matrigel containing growth factors to promote cell survival and recruit host blood vessels (see Methods). Under these conditions, no EP cell-derived tumors developed in 35 transplantations (FIG. 12B) over a period of 3-60 weeks. In contrast, when the cells from day 5 transient endoderm differentiation cultures of ESCs were transplanted in this system, all animals developed teratomas. Surprisingly, even purified CXCR4+CD117+ DE cells isolated by cell sorting from day 5 ESC differentiation cultures still generated tumors within 6 weeks of transplantation (FIG. 12B). It is possible that CXCR4+CD117+ DE cells may not be fully committed to endoderm and still retain teratoma forming ability or that a small number of contaminating ESCs present even after cell sorting led to tumor formation. In addition, when the cells from day 20 liver differentiation cultures of ESCs were transplanted, 4 out of 5 animals still developed teratomas (FIG. 12B). These data indicate that EP cells are less tumorigenic than ESCs, iPSCs, transient endoderm, and ESC-derived hepatic cultures.

Next, we examined transplanted matrigel-EP cell plugs for evidence of cellular differentiation. By 3-8 weeks after transplantation, cells formed various endodermal tissues, ranging from epithelium-forming cysts and tubes that appear similar to early gut tube endoderm (FIG. 12C, top panels) to larger, more complex structures containing differentiated cells (FIG. 12C, bottom panels; and data not shown). These included intestinal-like structures with epithelial cells surrounding a central lumen (FIG. 12C, bottom panels) and hepatoblast-like structures (data not shown). Staining with a pan-tissue human specific antibody demonstrated that these endodermal structures arose from the transplanted EP cells, in contrast to surrounding fat and mesenchyme, which was murine host-derived (FIG. 12D).

Immuno-histochemistry with human-specific antibodies was used to further characterize the developmental potential of transplanted EP cells. All EP cell-derived morphologically endodermal structures expressed FOXA1 and FOXA2, consistent with an endodermal origin (FIG. 12E and data not shown). The structures resembling intestinal epithelia expressed the transcription factors HNF4A and CDX2, key regulators of intestinal homeostasis (Spence et al., 2011). These cells also stained for the intestinal epithelial markers human fatty acid binding protein (IFABP), VILLIN1 and MUCIN2 (FIG. 12E). In addition, immunohistochemistry revealed that the hepatoblast/hepatocyte-like structures harbor cells positive for AFP and AAT (FIG. 12F). These data clearly demonstrate that EP cells are able to differentiate into gut epithelia and liver in vivo.

Discussion

The ability to generate stem cell lines that self-renew in vitro and differentiate into various mature tissues after manipulation of culture conditions or transplantation into animals has revolutionized biology and offers great promise for medical applications. In this regard, it is likely that different stem cell lines with distinct developmental potentials will be exploited for unique applications. For example, ESCs, trophectoderm stem (TS) cells, and extra-embryonic endoderm stem (XEN) cells, generated from three distinct cell types of the mouse blastocyst, display developmental potentials similar to their respective progenitors (Tanaka et al., 1998; Kunath et al., 2005). Here we describe the establishment of continuously replicating, clonal endoderm-committed stem cell lines from human ESCs and iPSCs. These cells, termed EP cells, are the first stem cell population to be described that can self-renew and specifically generate endodermal lineages from both the foregut and mid/hindgut.

EP cells exhibit several unique features in comparison to other endodermal progenitors previously reported. Hepatocyte stem cell populations can be derived from adult liver (Schmelzer et al., 2006). In addition, a possible hepatic stem cell population was generated from human ESCs (Zhao et al., 2009). These two cell types differentiate into liver lineages only, in contrast to the more broad developmental potential exhibited by EP cells. Another report indicates that SOX17 over-expression in human ESCs generates a progenitor population that expresses genes indicative of both ESCs and endoderm and can differentiate into endoderm derivatives (Seguin et al., 2008). These cells express ESC markers such as OCT4 and NANOG and are not endoderm-committed as they generate mesoderm-containing teratomas. A cell population similar to EP cells but derived from mouse ESCs has been reported (Morrison et al., 2008). Perhaps the most distinguishing feature of human EP cells described here is their extensive proliferative capacity. Mouse endoderm progenitors were only reported to expand 2000 fold in culture (Morrison et al., 2008), while human EP cells exhibit virtually unlimited self-renewal ($>10^{16}$)(FIG. 2 and data not shown). In contrast to the current study, mouse endoderm progenitors cells were not analyzed at the clonal level and were tested only for hepatic and pancreatic development and may therefore be restricted in developmental potential. In addition, EP cells can be maintained as a homogenous SOX17+FOXA1+ undifferentiated cell population. This is a critical point as partially differentiated EP cell cultures (see FIGS. 1 and 2A) cannot be reproducibly differentiated into either hepatocytes or β-cells at the efficiencies reported here, starting with pure undifferentiated EP cultures (data not shown and FIGS. 7 and 12). This is a well-known phenomenon also seen with directed differentiation of ESCs and may be due to the inability of partially differentiated cells to be re-specified down a different developmental path.

The ability of EP cells to generate glucose-responsive monohormonal insulin-expressing cells in vitro is promising (FIG. 7). Most attempts to generate functional β-cells from human PSCs in culture have failed to generate glucose responsive cells (D'Amour et al., 2006; Nostro et al., 2011). Those studies that have reported glucose responsiveness have either low levels of c-peptide+ cells and/or have not carefully examined the percentage of cells in a population with the abnormal polyhormonal phenotype (Jiang et al., 2007; Zhang et al. 2009; Thatava et al., 2010). It will be important in the future to compare β-cells generated using different methodologies to determine which generates the most robust functional cell type. In agreement with these prior studies, we also found that human ESCs stimulated to undergo pancreatic differentiation produce polyhormonal β-cells (data not shown and FIG. 7D). It is possible that production of functionally superior β-cells from EP cells reflects biological features related to the developmental timing of pancreatic endoderm production in vivo. During normal human embryogenesis, β-cells are not generated until ~10 weeks after endoderm specification (Spence and Wells, 2007) while in ESC differentiation cultures this typically occurs in ~2 weeks (D'Amour et al., 2006). It is possible that this accelerated timeframe in ESC differentiation cultures precludes the establishment of essential transcriptional networks and/or epigenetic modifications required for proper β-cell formation. Further analysis and comparison of ESC endoderm and EP cell differentiation cultures may reveal specific genes and epigenetic modifiers that regulate optimal formation of functional β-cells.

Our experiments indicate that EP cells lack intrinsic mesoderm and ectodermal potential. Directed differentiation protocols developed for mesoderm or ectoderm were unable to induce gene expression profiles specific to these lineages when applied to EP cells, suggesting an endoderm restricted program (FIG. 11). Moreover, in vivo transplanted EP cells exclusively generate endodermal structures that stained with a human specific antibody (FIG. 12D). In addition, pathological analysis of 24 independent transplants did not detect any morphologically ectodermal tissues (data not shown). This lineage restriction makes EP cells a powerful platform to dissect the signals necessary for the specification of endodermal cell types.

Flow cytometry and microarray analyses reveal a unique gene expression pattern in human EP cells, distinct from undifferentiated ESCs or CXCR4+CD117+ transient endoderm. LHX1 and EOMES, while not typically defined as mature gut tube markers are maintained in EP cells (FIG. 5). This raises the possibility that these transcription factors may play a role in EP cell fate or self-renewal. These data along with the expression of markers typical of cells undergoing specification of various endodermal lineages (Table 1) suggest that EP cells are not gut tube endoderm "frozen in time", but are a distinct in vitro stem cell population. Investigation of these differences could identify key regulators of endoderm maintenance and development.

In summary, we describe a simple culture procedure to reproducibly and efficiently generate endoderm stem cell lines from human PSCs. Resultant EP cells self-renew rapidly and can be stimulated to form hepatic, pancreatic and intestinal tissues. Moreover, EP cells are nontumorigenic, reflecting their potential utility for tissue replacement therapies. Our work challenges the notion that ESCs/iPSCs must be used as a starting point for directed tissue differentiation studies. Rather, EP cells serve as an intermediate between iPSCs/ESCs and mature endodermal derivatives. The ability to generate functional mono-hormonal β-cells from iPSCs will enable in vitro modeling of diseases of the beta cell, including multiple genetic forms of diabetes and hyperinsulinemias. These lines will provide innovative experimental platforms to investigate mechanisms of endodermal differentiation and a safer, more efficient starting point for tissue replacement therapies aimed at common human disorders including liver failure and diabetes.

REFERENCES FOR EXAMPLE I

Ahlgren, U., Pfaff, S. L., Jessell, T. M., Edlund, T., and Edlund, H. (1997). Independent requirement for ISL1 in formation of pancreatic mesenchyme and islet cells. Nature 385, 257-260.

Ang, S. L., Wierda, A., Wong, D., Stevens, K. A., Cascio, S., Rossant, J., and Zaret, K. S. (1993). The formation and maintenance of the definitive endoderm lineage in the mouse: involvement of HNF3/forkhead proteins. Development 119, 1301-1315.

Barker, N., Huch, M., Kujala, P., van de Wetering, M., Snippert, H. J., van Es, J. H., Sato, T., Stange, D. E., Begthel, H., van den Born, M., et al. (2010) Lgr5(+ve) stem cells drive self renewal in the stomach and build long-lived gastric units in vitro. Cell Stem Cell 6, 25-36.

Basma, H., Soto-Gutierrez, A., Yannam, G. R., Liu, L., Ito, R., Yamamoto, T., Ellis, E., Carson, S. D., Sato, S., Chen, Y., et al. (2009). Differentiation and transplantation of human embryonic stem cell-derived hepatocytes. Gastroenterology 136, 990-999.

Bowen, M. A., Patel, D. D., Li, X., Modrell, B., Malacko, A. R., Wang, W. C., Marquardt, H., Neubauer, M., Pesando, J. M., Francke, U., et al. (1995). Cloning, mapping, and characterization of activated leukocyte-cell adhesion molecule (ALCAM), a CD6 ligand. J Exp Med 181, 2213-2220.

Choi, M. Y., Romer, A. I., Hu, M., Lepourcelet, M., Mechoor, A., Yesilaltay, A., Krieger, M., Gray, P. A., and Shivdasani, R. A. (2006). A dynamic expression survey identifies transcription factors relevant in mouse digestive tract development. Development 133, 4119-4129.

D'Amour, K. A., Agulnick, A. D., Eliazer, S., Kelly, O. G., Kroon, E., and Baetge, E. E. (2005). Efficient differentiation of human embryonic stem cells to definitive endoderm. Nat Biotechnol 23, 1534-1541.

D'Amour, K. A., Bang, A. G., Eliazer, S., Kelly, O. G., Agulnick, A. D., Smart, N. G., Moorman, M. A., Kroon, E., Carpenter, M. K., and Baetge, E. E. (2006). Production of pancreatic hormone expressing endocrine cells from human embryonic stem cells. Nat Biotechnol 24, 1392-1401.

Duncan, S. A., Nagy, A., and Chan, W. (1997). Murine gastrulation requires HNF-4 regulated gene expression in the visceral endoderm: tetraploid rescue of Hnf-4(-/-) embryos. Development 124, 279-287.

Gadue, P., Huber, T. L., Paddison, P. J., and Keller, G. M. (2006). Wnt and TGF-beta signaling are required for the induction of an in vitro model of primitive streak formation using embryonic stem cells. Proc Natl Acad Sci USA 103, 16806-16811.

Gouon-Evans, V., Boussemart, L., Gadue, P., Nierhoff, D., Koehler, C. I., Kubo, A., Shafritz, D. A., and Keller, G. (2006). BMP-4 is required for hepatic specification of mouse embryonic stem cell-derived definitive endoderm. Nat Biotechnol 24, 1402-1411.

Greber, B., Coulon, P., Zhang, M., Moritz, S., Frank, S., Muller-Molina, A. J., Arauzo-Bravo, M. J., Han, D. W., Pape, H. C., and Scholer, H. R. FGF signalling inhibits neural induction in human embryonic stem cells. EMBO J. 30, 4874-4884.

Hentze, H., Soong, P. L., Wang, S. T., Phillips, B. W., Putti, T. C., and Dunn, N. R. (2009). Teratoma formation by human embryonic stem cells: evaluation of essential parameters for future safety studies. Stem Cell Res 2, 198-210.

Herrera, P. L. (2000). Adult insulin- and glucagon-producing cells differentiate from two independent cell lineages. Development 127, 2317-2322.

Jiang, J., Au, M., Lu, K., Eshpeter, A., Korbutt, G., Fisk, G., and Majumdar, A. S. (2007). Generation of insulin-producing islet-like clusters from human embryonic stem cells. Stem Cells 25, 1940-1953.

Kanai-Azuma, M., Kanai, Y., Gad, J. M., Tajima, Y., Taya, C., Kurohmaru, M., Sanai, Y., Yonekawa, H., Yazaki, K., Tam, P. P., et al. (2002). Depletion of definitive gut endoderm in Sox17-null mutant mice. Development 129, 2367-2379.

Kunath, T., Arnaud, D., Uy, G. D., Okamoto, I., Chureau, C., Yamanaka, Y., Heard, E., Gardner, R. L., Avner, P., and Rossant, J. (2005). Imprinted X-inactivation in extra-embryonic endoderm cell lines from mouse blastocysts. Development 132, 1649-1661.

Lu, C. C., Brennan, J., and Robertson, E. J. (2001). From fertilization to gastrulation: axis formation in the mouse embryo. Curr Opin Genet Dev 11, 384-392.

Ludtke, T. H., Christoffels, V. M., Petry, M., and Kispert, A. (2009). Tbx3 promotes liver bud expansion during mouse development by suppression of cholangiocyte differentiation. Hepatology 49, 969-978.

Lukowiak, B., Vandewalle, B., Riachy, R., Kerr-Conte, J., Gmyr, V., Belaich, S., Lefebvre, J., and Pattou, F. (2001). Identification and purification of functional human beta-cells by a new specific zinc-fluorescent probe. J Histochem Cytochem 49, 519-528.

Mizrak, D., Brittan, M., and Alison, M. R. (2008). CD133: molecule of the moment. J Pathol 214, 3-9.

Morrison, G. M., Oikonomopoulou, I., Migueles, R. P., Soneji, S., Livigni, A., Enver, T., and Brickman, J. M. (2008). Anterior definitive endoderm from ESCs reveals a role for FGF signaling. Cell Stem Cell 3, 402-415.

Murry, C. E., and Keller, G. (2008). Differentiation of embryonic stem cells to clinically relevant populations: lessons from embryonic development. Cell 132, 661-680.

Nostro, M. C., Sarangi, F., Ogawa, S., Holtzinger, A., Corneo, B., Li, X., Micallef, S. J., Park, I. H., Basford, C., Wheeler, M. B., et al. (2011). Stage-specific signaling through TGFbeta family members and WNT regulates patterning and pancreatic specification of human pluripotent stem cells. Development 138, 861-871.

Rezania, A., Riedel, M. J., Wideman, R. D., Karanu, F., Ao, Z., Warnock, G. L., and Kieffer, T. J. (2011) Production of functional glucagon-secreting alpha-cells from human embryonic stem cells. Diabetes 60, 239-247.

Schmelzer, E., Wauthier, E., and Reid, L. M. (2006). The phenotypes of pluripotent human hepatic progenitors. Stem Cells 24, 1852-1858.

Seguin, C. A., Draper, J. S., Nagy, A., and Rossant, J. (2008). Establishment of endoderm progenitors by SOX transcription factor expression in human embryonic stem cells. Cell Stem Cell 3, 182-195.

Sherwood, R. I., Jitianu, C., Cleaver, O., Shaywitz, D. A., Lamenzo, J. O., Chen, A. E., Golub, T. R., and Melton, D. A. (2007). Prospective isolation and global gene expression analysis of definitive and visceral endoderm. Dev Biol 304, 541-555.

Shu, W., Yang, H., Zhang, L., Lu, M. M., and Morrisey, E. E. (2001). Characterization of a new subfamily of winged-helix/forkhead (Fox) genes that are expressed in the lung and act as transcriptional repressors. J Biol Chem 276, 27488-27497.

Smith, S. B., Qu, H. Q., Taleb, N., Kishimoto, N. Y., Scheel, D. W., Lu, Y., Patch, A. M., Grabs, R., Wang, J., Lynn, F. C., et al. (2010) Rfx6 directs islet formation and insulin production in mice and humans. Nature 463, 775-780.

Spence, J. R., and Wells, J. M. (2007). Translational embryology: using embryonic principles to generate pancreatic endocrine cells from embryonic stem cells. Dev Dyn 236, 3218-3227.

Spence, J. R., Lange, A. W., Lin, S. C., Kaestner, K. H., Lowy, A. M., Kim, I., Whitsett, J. A., and Wells, J. M. (2009). Sox17 regulates organ lineage segregation of ventral foregut progenitor cells. Dev Cell 17, 62-74.

Spence, J. R., Mayhew, C. N., Rankin, S. A., Kuhar, M. F., Vallance, J. E., Tolle, K., Hoskins, E. E., Kalinichenko, V. V., Wells, S. I., Zorn, A. M., et al. (2011). Directed differentiation of human pluripotent stem cells into intestinal tissue in vitro. Nature 470, 105-109.

Spence, J. R., Lauf, R., and Shroyer, N. F. (2011). Vertebrate intestinal endoderm development. Dev Dyn 240, 501-520.

Stadtfeld, M., and Hochedlinger, K. (2010). Induced pluripotency: history, mechanisms, and applications. Genes Dev 24, 2239-2263.

Stroncek, D. F. (2007). Neutrophil-specific antigen HNA-2a, NB1 glycoprotein, and CD177. Curr Opin Hematol 14, 688-693.

Tanaka, S., Kunath, T., Hadjantonakis, A. K., Nagy, A., and Rossant, J. (1998). Promotion of trophoblast stem cell proliferation by FGF4. Science 282, 2072-2075.

Thatava, T., Nelson, T. J., Edukulla, R., Sakuma, T., Ohmine, S., Tonne, J. M., Yamada, S., Kudva, Y., Terzic, A., and Ikeda, Y. (2010). Indolactam V/GLP-1-mediated differentiation of human iPS cells into glucose-responsive insulin-secreting progeny. Gene Ther 18, 283-293.

Varlakhanova, N. V., Cotterman, R. F., deVries, W. N., Morgan, J., Donahue, L. R., Murray, S., Knowles, B. B., and Knoepfler, P. S. (2010) Myc maintains embryonic stem cell pluripotency and self-renewal. Differentiation 80, 9-19.

Zaret, K. S., and Grompe, M. (2008). Generation and regeneration of cells of the liver and pancreas. Science 322, 1490-1494.

Zhang, D., Jiang, W., Liu, M., Sui, X., Yin, X., Chen, S., Shi, Y., and Deng, H. (2009). Highly efficient differentiation of human ES cells and iPS cells into mature pancreatic insulin-producing cells. Cell Res 19, 429-438.

Zhao, D., Chen, S., Cai, J., Guo, Y., Song, Z., Che, J., Liu, C., Wu, C., Ding, M., and Deng, H. (2009). Derivation and characterization of hepatic progenitor cells from human embryonic stem cells. PLoS One 4, e6468.

Zorn, A. M., and Wells, J. M. (2009). Vertebrate endoderm development and organ formation. Annu Rev Cell Dev Biol 25, 221-251.

EXAMPLE II

Large Scale Growth of Endodermal Progenitor Cells in Bioreactor Culture

In Example I, we described a method to expand endoderm derived from human pluripotent stem cells, generating endoderm stem cell lines that we term endodermal progenitor (EP) cells (Cheng et al., 2012). EP cells can be expanded in culture at least $10^{16}$ fold while maintaining the ability to differentiate into endodermal lineages both in vitro and in vivo using mouse models. In addition, using a directed differentiation protocol we found that EP cells generate mono-hormonal and glucose-responsive beta like cells in vitro. This is in stark contrast to pluripotent stem cells which typically generate non-functional beta like cells that co-express multiple endocrine hormones such as insulin, glucagon, and somatostatin in the same cell (D' Amour et al., 2006). Our initial protocol relied upon an adherent cell culture system that was not amenable to large-scale expansion. We have adapted our initial culture conditions to be able to grow EP cells in spinner flask bioreactor cultures that allow large-scale expansion of EP cells.

The following materials and methods are provided to facilitate the practice of Example II.

Medium Recipes:

Serum Free Differentiation Media (SFD):

Add the reagents listed below to approximately 1 liter without growth factors (stable approximately 2 weeks at 4° C. in dark once made and stored in bottle covered in tin foil):

| Ingredient | Volume | Source |
|---|---|---|
| Home-made IMDM* | 750 ml | Invitrogen: 12200-036 |
| Ham's F12 | 250 ml | Cellgro cat#: 10-080-CV |
| N2 | 5 ml | Gibco cat#: 17502-048 |
| B27 w/o retinoic acid | 10 ml | Gibco cat#: 12587-010 |
| 10% BSA** in PBS | 5 ml | Sigma A1470 |

EP Cell Basic Media (4 Factor Media):
Add the following reagents fresh each day to SFD.

| Basic Media SFD | | | |
|---|---|---|---|
| Ingredient | Stock | Volume | Final |
| MTG (Sigma) | 13 ul/ml | 3 ul/ml | 4.5 × 10−4 M |
| Ascorbic Acid* | 5 mg/ml | 10 ul/ml | 50 ug/ml |
| Human EGF | 50 ug/ml | 0.2 ul/ml | 10 ng/ml |
| Human BMP4 | 100 ug/ml | 0.5 ul/ml | 50 ng/ml |
| Human bFGF | 10 ug/ml | 1 ul/ml | 10 ng/ml |
| Human VEGF | 50 ug/ml | 0.2 ul/ml | 10 ng/ml |

*L-Ascorbic Acid Phosphate Magnesium (Wako, cat# 013-19641)

Thawing:

Endoderm progenitor (EP) cells are thawed in a water bath at 37° C. from a frozen vial stored in liquid nitrogen. Depending on cell number, the thawed cells are either plated in adherent culture or directly into a spinner flask. To thaw cells directly into a spinner flask, 4.5-6 million cells are plated along with 0.75 million swiss webster mouse embryonic fibroblasts (mefs/feeders) (irradiated at p3).

Thaw undiluted matrigel from BD LIFESCIENCES on ice. Use cold pipettes/tips (stored at −20° C.) while handling matrigel.

Wash the thawed cells and mefs together in a 50 ml falcon tube filled with wash media (Iscove's Modified Dulbecco's Medium (IMDM)+1% L-glutamine (L-glu)+1% Penicillin Streptomycin (P/S)). Centrifuge at 1400 rpm for 5 minutes. Aspirate the wash media to obtain a pellet of thawed cells and mefs.

Plating and Culturing EP Cells in Spinner Flask:

At the outset, prepare 60 ml of 4 Factor media, divide into 30 ml aliquots in 2 separate 50 ml corning tubes, and place in a water bath at 37° C.

Put the 50 ml tube with cells on ice for 2-5 minutes to ensure that the pellet becomes chilled.

Using a 5 ml chilled pipette, resuspend the cold pellet in 2 ml of undiluted matrigel (keeping pipetteman on slow/medium). Make sure the pellet is resuspended in the matrigel by pipetting up and down 3-4 times ensuring no large aggregates are visible.

Add 1 ml of the cell pellet imbedded in matrigel drop by drop to each of the warmed 30 ml media aliquots. Shake the tube as each drop of matrigel falls into the media to ensure that the cell/matrigel mixture polymerizes into uniform sized aggregates.

Let the tubes stand at room temperature for 2-3 minutes. Transfer the media from both tubes into a 125 ml spinner flask (corning) using a 25 ml pipette and pipetting up and down at least twice before transferring. Spinner flasks are maintained in a 5% $CO_2$ 5% $O_2$ incubator on a magnetic stirrer base set at 75 rpm.

The cultures are then fed with 60 ml of 4 factor media on day 2, replacing 45 ml of the spent media. Ensure that any cells/matrigel floats carried over in the spent media are centrifuged, resuspended and added back to the flask.

Repeat the feed on day 4 using 60 ml of 4 factor media. Split cells on day 5. Some cell lines have a slower growth rate and harvesting cultures on day 6 helps to increase the final cell yield (typically 3-5 fold expansion). This system is scalable to 300 ml cultures using a 500 ml spinner flask, using a linear scaling of all cells/reagents for the larger volume culture.

Splitting and Freezing EP Cells from Spinner Flask:

Aliquot 6 ml of 0.25% trypsin EDTA into a 14 ml tube and warm to 370 C.

On day 5 take the entire culture and transfer it into two 50 ml V-bottom corning tubes (equal volumes).

Centrifuge the tubes at 1600 rpm for 5 minutes. Aspirate off the spent media.

Resuspend both the pellets thoroughly in 6 ml of warmed 0.25% trypsin EDTA and combine them in one tube. Place the tube in a water bath at 37° C. for 6 minutes. Vortex the tube every 2 minutes to ensure the cell pellet is still resuspended in the trypsin.

Add 3 ml of serum after 6 minutes to stop trypsin action. Pipette up and down vigorously at least 5 times at this step to obtain a single cell suspension.

Fill the tube up to 50 ml using wash media. Centrifuge the cells at 2000 rpm for 5 minutes.

Resuspend the cell pellet in 3-5 ml of 4 factor media using a p1000 and pipette vigorously 10-20 times to ensure single cells.

Count the cells, and replate using new matrigel, mefs and 4 factor media as described above.

For freezing: Make a mixture of 80% FBS and 20% DMSO in a separate tube. Bring the cell count to 12.5 million cells/ml. Add 600 μl of the FBS-DMSO mix to 400 μl of cells and put it into cryovials prechilled at −200 C. (1.5 ml of FBS-DMSO mix per ml of cells in 4 factor media to make final concentration of 5 million cells/ml or vial.)

Establishing an EP Cell Line in Spinner Flask Culture

Embryonic stem cells are differentiated to endoderm as previously described (Cheng et al., 2012)

These cells are then harvested after day 5 or day 6, stained CXCR-4-PE AND CD117-APC, and sorted for a high double positive population These cells are then washed and pellet together with 0.75 million mefs post-sort. Final cell number after sort is usually between 1-2 million post-sort and initial cell number is between 5-15 million cells from 3 10 cm dishes. (cell number varies from cell line to cell line)

This cell pellet is homogenized in 2 ml of matrigel and plated into 60 ml of pre-warmed basic EPC media as described above.

Results

EP cell lines derived from the human ES cell line H9 and the wild-type induced pluripotent stem (iPS) cell line WT2.2 (Mills et al., 2013) were grown in spinner flask culture using an adaptation of the adherent conditions used to expand EP cells (see materials and methods section). To adapt EP cells to non-adherent culture we embedded EP cells and mouse embryonic fibroblast feeders in cold matrigel and added this mixture to warm EP cell culture media that we had previously described. The EP cell cells form rafts of matrigel with embedded cells which are maintained in non-adherent conditions. Initial experiments used 125 ml spinner flasks with a 60-75 ml working volume. Both EP cell lines maintained expression of EP cell markers by flow cytometry (FIG. 13A) and maintain normal EP cell morphology (FIG. 13B). Gene expression analysis by QRT-PCR showed that in spinner flask cultures maintained SOX17 and EOMES at similar levels to control cultures maintained on adherent tissue culture dishes (FIG. 13C). No cultures expressed the ES/iPS cell marker OCT4. EP cells cultured in spinner flask culture also demonstrated a growth rate similar to cell grown on adherent culture, with approximately 100 million fold expansion in 13-15 passages (FIG. 13D).

To demonstrate that these cultures could be scaled to large spinner flask sizes, we also expanded the H9 EP cell line in a 500 ml spinner flask. EP cells maintained endodermal marker expression by both flow cytometry and QRT-PCR and maintained normal EP cell morphology (FIGS. 14A, 14B and 14C). These cultures were maintained for two passages with similar growth rate of EP cells in the smaller spinner flask and could generate approximately 150 million EP cells in a 300 ml working cell culture volume.

Lastly, we wanted to demonstrate the EP cells expanded long term in spinner flask non-adherent culture maintained the ability to differentiate into mono-hormonal pancreatic beta like cells. Utilizing our previously published differentiation protocol, we show the EP cells expanded for greater than 10 passages in spinner flask culture still efficiency generate mono-hormonal beta like cells (FIG. 15). Flow cytometry demonstrates robust expression of c-peptide (~30%) as a surrogate for insulin expression while no expression of the alpha cell hormone glucagon is seen.

REFERENCES FOR EXAMPLE II

Cheng, X., Ying, L., Lu, L., Galvão, A. M., Mills, J. A., Lin, H. C., . . . Gadue, P. (2012). Self-renewing endodermal progenitor lines generated from human pluripotent stem cells. Cell Stem Cell, 10(4), 371-384. doi: 10.1016/j.stem.2012.02.024

D' Amour, K. A., Bang, A. G., Eliazer, S., Kelly, O. G., Agulnick, A. D., Smart, N. G., Baetge, E. E. (2006). Production of pancreatic hormone-expressing endocrine cells from human embryonic stem cells. Nature biotechnology, 24(11), 1392-1401. doi: 10.1038/nbt1259

Mills, J. A., Wang, K., Paluru, P., Ying, L., Lu, L., Galvão, A. M., . . . Gadue, P. (2013). Clonal genetic and hematopoietic heterogeneity among human induced pluripotent stem cell lines. Blood, 13(6), 663-675. doi: 10.1182/blood-2013-02-484444

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for the production of functional, non-tumorigenic, self-renewing, multipotent endodermal progenitor (EP) cells comprising, contacting stem cells with Activin A in serum free differentiation medium thereby inducing formation of definite endoderm (DE) cells; and culturing DE cells in the presence of BMP4, VEGF, bFGF, and EGF or homologs thereof, wherein said EP cells are grown in spinner flask culture, comprising;
   a) embedding a mixed culture of said stem cells and mouse embryonic fibroblasts (MEFs) in a biocompatible matrix;
   b) adding said stem cell containing matrix to warmed EP culture medium, said EP medium being serum free differentiation medium comprising Activin A in an amount effective to induce formation of definite endoderm (DE) cells;
   c) culturing DE cells in a spinner flask and culturing DE cells in the presence of a TGF-beta inducing agent, under conditions suitable for rafts of matrix containing EP cells to form, said culture being non-adherent; said EP cells maintaining expression of EP cells markers and normal EP cell morphology; and
   d) optionally harvesting said EP cells for further treatment or culture and/or freezing said EP cells obtained from step c).

2. The method of 1, wherein said cells express SOX17, FOXA2, and HNF4A and lack OCT4 or NANOG.

3. The method of claim 2, wherein said EP cells are induced to differentiate into endodermal tissues.

4. The method of claim 1, wherein said biocompatible matrix is matrigel.

5. The method of claim 1, wherein said EP cells can be expanded 100-million fold in 13-15 passages in a 125 ml spinner flask.

6. The method of claim 1, wherein 150 million EP cells are generated from a 300 ml working cell culture volume after two passages in a 500 ml spinner flask.

7. A method for the production of functional, non-tumorigenic, self-renewing, multipotent endodermal progenitor (EP) cells comprising, contacting stem cells with Activin A in serum free differentiation medium thereby inducing formation of definite endoderm (DE) cells; and culturing DE cells in the presence of BMP4, VEGF, bFGF, and EGF or homologs thereof in liquid media or biocompatible matrix and optionally a fibroblast feeder layer; thereby producing EP cells, wherein said media or biocompatible matrix further comprises TGF-beta or a TGF-beta inducing agent.

* * * * *

SEQUENCE LISTING

```
<160> NUMBER OF SEQ ID NOS: 52

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
agggcctgaa gctagtggat aagt                                              24

<210> SEQ ID NO 2
<211> LENGTH: 24
<212> TYPE: DNA
<213> ORGANISM: Artificial Sequence
<220> FEATURE:
<223> OTHER INFORMATION: Primer

<400> SEQUENCE: 2
tctgtttctt ggcctcttcg gtgt                                              24

<210> SEQ ID NO 3
<211> LENGTH: 26
<212> TYPE: DNA
<213> ORGANISM: Artificial Sequence
<220> FEATURE:
<223> OTHER INFORMATION: Primer

<400> SEQUENCE: 3
ctacctgcct ttctggaaga actttg                                            26

<210> SEQ ID NO 4
<211> LENGTH: 24
<212> TYPE: DNA
```

```
<213> ORGANISM: Artificial Sequence
<220> FEATURE:
<223> OTHER INFORMATION: Primer

<400> SEQUENCE: 4
tctgtttctt ggcctcttcg gtgt                                           24

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
gtgaaacaca agcccaaggc aaca                                           24

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
tcctcggcaa agcaggtctc                                                20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
aggactgtgc ccacttcacc                                                20

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
tggccttgtc cagctctgtc t                                              21

<210> SEQ ID NO 9
<211> LENGTH: 25
<212> TYPE: DNA
<213> ORGANISM: Artificial Sequence
<220> FEATURE:
<223> OTHER INFORMATION: Primer

<400> SEQUENCE: 9
tcctggtctg ggaagggaag agaaa                                          25

<210> SEQ ID NO 10
<211> LENGTH: 25
<212> TYPE: DNA
<213> ORGANISM: Artificial Sequence
<220> FEATURE:
<223> OTHER INFORMATION: Primer

<400> SEQUENCE: 10
cggaagccaa aggcagctaa gatag                                          25
```

<210> SEQ ID NO 11
<211> LENGTH: 26
<212> TYPE: DNA
<213> ORGANISM: Artificial Sequence
<220> FEATURE:
<223> OTHER INFORMATION: Primer

<400> SEQUENCE: 11
gaagagtgcg atcaagaacc catgac        26

<210> SEQ ID NO 12
<211> LENGTH: 27
<212> TYPE: DNA
<213> ORGANISM: Artificial Sequence
<220> FEATURE:
<223> OTHER INFORMATION: Primer

<400> SEQUENCE: 12
gtctctcctc cttctcctcc tatcttt        27

<210> SEQ ID NO 13
<211> LENGTH: 25
<212> TYPE: DNA
<213> ORGANISM: Artificial Sequence
<220> FEATURE:
<223> OTHER INFORMATION: Primer

<400> SEQUENCE: 13
gtgaccaaat cagtgtgagg aggta        25

<210> SEQ ID NO 14
<211> LENGTH: 25
<212> TYPE: DNA
<213> ORGANISM: Artificial Sequence
<220> FEATURE:
<223> OTHER INFORMATION: Primer

<400> SEQUENCE: 14
aggaggagtt aatggtgcta actgg        25

<210> SEQ ID NO 15
<211> LENGTH: 24
<212> TYPE: DNA
<213> ORGANISM: Artificial Sequence
<220> FEATURE:
<223> OTHER INFORMATION: Primer

<400> SEQUENCE: 15
acccttggga agtggaccca gaaa        24

<210> SEQ ID NO 16
<211> LENGTH: 26
<212> TYPE: DNA
<213> ORGANISM: Artificial Sequence
<220> FEATURE:
<223> OTHER INFORMATION: Primer

<400> SEQUENCE: 16
agaagttctg aaggactctg actaga        26

<210> SEQ ID NO 17
<211> LENGTH: 20
<212> TYPE: DNA
<213> ORGANISM: Artificial Sequence
<220> FEATURE:

<223> OTHER INFORMATION: Primer

<400> SEQUENCE: 17
cccgtccaag gccaagaaga                                              20

<210> SEQ ID NO 18
<211> LENGTH: 26
<212> TYPE: DNA
<213> ORGANISM: Artificial Sequence
<220> FEATURE:
<223> OTHER INFORMATION: Primer

<400> SEQUENCE: 18
tgacgatgag cgcgatgtag gaatag                                       26

<210> SEQ ID NO 19
<211> LENGTH: 24
<212> TYPE: DNA
<213> ORGANISM: Artificial Sequence
<220> FEATURE:
<223> OTHER INFORMATION: Primer

<400> SEQUENCE: 19
taccgcactc ttgcagaagg acaa                                         24

<210> SEQ ID NO 20
<211> LENGTH: 26
<212> TYPE: DNA
<213> ORGANISM: Artificial Sequence
<220> FEATURE:
<223> OTHER INFORMATION: Primer

<400> SEQUENCE: 20
tgcacgtctt tgactccttg aaaccc                                       26

<210> SEQ ID NO 21
<211> LENGTH: 24
<212> TYPE: DNA
<213> ORGANISM: Artificial Sequence
<220> FEATURE:
<223> OTHER INFORMATION: Primer

<400> SEQUENCE: 21
ttcccagaag aggtcgccat tgtt                                         24

<210> SEQ ID NO 22
<211> LENGTH: 26
<212> TYPE: DNA
<213> ORGANISM: Artificial Sequence
<220> FEATURE:
<223> OTHER INFORMATION: Primer

<400> SEQUENCE: 22
caaccagttt ataaagtccc tggcgg                                       26

<210> SEQ ID NO 23
<211> LENGTH: 25
<212> TYPE: DNA
<213> ORGANISM: Artificial Sequence
<220> FEATURE:
<223> OTHER INFORMATION: Primer

<400> SEQUENCE: 23
tccaacccaa cctcatcctc cttct                                        25

<210> SEQ ID NO 24
<211> LENGTH: 24
<212> TYPE: DNA
<213> ORGANISM: Artificial Sequence
<220> FEATURE:
<223> OTHER INFORMATION: Primer

<400> SEQUENCE: 24
tcctctccac tccaagttcc tgtt                                        24

<210> SEQ ID NO 25
<211> LENGTH: 23
<212> TYPE: DNA
<213> ORGANISM: Artificial Sequence
<220> FEATURE:
<223> OTHER INFORMATION: Primer

<400> SEQUENCE: 25
tttgtgaacc aacacctgtg cgg                                         23

<210> SEQ ID NO 26
<211> LENGTH: 24
<212> TYPE: DNA
<213> ORGANISM: Artificial Sequence
<220> FEATURE:
<223> OTHER INFORMATION: Primer

<400> SEQUENCE: 26
gcgggtcttg ggtgtgtaga agaa                                        24

<210> SEQ ID NO 27
<211> LENGTH: 26
<212> TYPE: DNA
<213> ORGANISM: Artificial Sequence
<220> FEATURE:
<223> OTHER INFORMATION: Primer

<400> SEQUENCE: 27
tatctgacac ctcagcttcc tccagt                                      26

<210> SEQ ID NO 28
<211> LENGTH: 24
<212> TYPE: DNA
<213> ORGANISM: Artificial Sequence
<220> FEATURE:
<223> OTHER INFORMATION: Primer

<400> SEQUENCE: 28
tgttacgcac ggtctctggg attt                                        24

<210> SEQ ID NO 29
<211> LENGTH: 24
<212> TYPE: DNA
<213> ORGANISM: Artificial Sequence
<220> FEATURE:
<223> OTHER INFORMATION: Primer

<400> SEQUENCE: 29
tttggacaag ggagacctgg agaa                                        24

<210> SEQ ID NO 30
<211> LENGTH: 25
<212> TYPE: DNA
<213> ORGANISM: Artificial Sequence
<220> FEATURE:
<223> OTHER INFORMATION: Primer

```
<400> SEQUENCE: 30
agaggagaag gacaagaaag ccaca                                          25

<210> SEQ ID NO 31
<211> LENGTH: 23
<212> TYPE: DNA
<213> ORGANISM: Artificial Sequence
<220> FEATURE:
<223> OTHER INFORMATION: Primer

<400> SEQUENCE: 31
ggccaaatgg gagagtggtt aca                                            23

<210> SEQ ID NO 32
<211> LENGTH: 24
<212> TYPE: DNA
<213> ORGANISM: Artificial Sequence
<220> FEATURE:
<223> OTHER INFORMATION: Primer

<400> SEQUENCE: 32
ttgccatcat tacaccagta gcgg                                           24

<210> SEQ ID NO 33
<211> LENGTH: 18
<212> TYPE: DNA
<213> ORGANISM: Artificial Sequence
<220> FEATURE:
<223> OTHER INFORMATION: Primer

<400> SEQUENCE: 33
tgcagcagcg gcacattc                                                  18

<210> SEQ ID NO 34
<211> LENGTH: 26
<212> TYPE: DNA
<213> ORGANISM: Artificial Sequence
<220> FEATURE:
<223> OTHER INFORMATION: Primer

<400> SEQUENCE: 34
cgccagcttc tcgtatttct ccttgt                                         26

<210> SEQ ID NO 35
<211> LENGTH: 26
<212> TYPE: DNA
<213> ORGANISM: Artificial Sequence
<220> FEATURE:
<223> OTHER INFORMATION: Primer

<400> SEQUENCE: 35
ctgctcaagt tcgacgtgaa gaagga                                         26

<210> SEQ ID NO 36
<211> LENGTH: 24
<212> TYPE: DNA
<213> ORGANISM: Artificial Sequence
<220> FEATURE:
<223> OTHER INFORMATION: Primer

<400> SEQUENCE: 36
tagttgctcg ccatccagta caga                                           24

<210> SEQ ID NO 37
<211> LENGTH: 24
```

```
<212> TYPE: DNA
<213> ORGANISM: Artificial Sequence
<220> FEATURE:
<223> OTHER INFORMATION: Primer

<400> SEQUENCE: 37
tgcagtgtga tgtctctgtt gggt                                              24

<210> SEQ ID NO 38
<211> LENGTH: 24
<212> TYPE: DNA
<213> ORGANISM: Artificial Sequence
<220> FEATURE:
<223> OTHER INFORMATION: Primer

<400> SEQUENCE: 38
atccatgggc cagcaacaat tgac                                              24

<210> SEQ ID NO 39
<211> LENGTH: 25
<212> TYPE: DNA
<213> ORGANISM: Artificial Sequence
<220> FEATURE:
<223> OTHER INFORMATION: Primer

<400> SEQUENCE: 39
cccatggtgg gttgtcatat attca                                             25

<210> SEQ ID NO 40
<211> LENGTH: 24
<212> TYPE: DNA
<213> ORGANISM: Artificial Sequence
<220> FEATURE:
<223> OTHER INFORMATION: Primer

<400> SEQUENCE: 40
ccagcatcac atctcaaaca gcac                                              24

<210> SEQ ID NO 41
<211> LENGTH: 24
<212> TYPE: DNA
<213> ORGANISM: Artificial Sequence
<220> FEATURE:
<223> OTHER INFORMATION: Primer

<400> SEQUENCE: 41
tcactcaagt ctgtctgcct ctca                                              24

<210> SEQ ID NO 42
<211> LENGTH: 24
<212> TYPE: DNA
<213> ORGANISM: Artificial Sequence
<220> FEATURE:
<223> OTHER INFORMATION: Primer

<400> SEQUENCE: 42
aaatcccgga cctgattggg agta                                              24

<210> SEQ ID NO 43
<211> LENGTH: 21
<212> TYPE: DNA
<213> ORGANISM: Artificial Sequence
<220> FEATURE:
<223> OTHER INFORMATION: Primer

<400> SEQUENCE: 43
```

-continued gcatgaacat gagcggcatg g                                         21

<210> SEQ ID NO 44
<211> LENGTH: 23
<212> TYPE: DNA
<213> ORGANISM: Artificial Sequence
<220> FEATURE:
<223> OTHER INFORMATION: Primer

<400> SEQUENCE: 44
gccgacaggt acttctgttg ctt                                       23

<210> SEQ ID NO 45
<211> LENGTH: 26
<212> TYPE: DNA
<213> ORGANISM: Artificial Sequence
<220> FEATURE:
<223> OTHER INFORMATION: Primer

<400> SEQUENCE: 45
aggacgacga ctacaataag cctctg                                    26

<210> SEQ ID NO 46
<211> LENGTH: 21
<212> TYPE: DNA
<213> ORGANISM: Artificial Sequence
<220> FEATURE:
<223> OTHER INFORMATION: Primer

<400> SEQUENCE: 46
cgctgctgga cttgtgcttc t                                         21

<210> SEQ ID NO 47
<211> LENGTH: 25
<212> TYPE: DNA
<213> ORGANISM: Artificial Sequence
<220> FEATURE:
<223> OTHER INFORMATION: Primer

<400> SEQUENCE: 47
ctccaccttg ggacctgttt agaga                                     25

<210> SEQ ID NO 48
<211> LENGTH: 25
<212> TYPE: DNA
<213> ORGANISM: Artificial Sequence
<220> FEATURE:
<223> OTHER INFORMATION: Primer

<400> SEQUENCE: 48
cgcccgagta agaatggctt tatgg                                     25

<210> SEQ ID NO 49
<211> LENGTH: 26
<212> TYPE: DNA
<213> ORGANISM: Artificial Sequence
<220> FEATURE:
<223> OTHER INFORMATION: Primer

<400> SEQUENCE: 49
gagaatgatg ccctggaacc tgaaga                                    26

<210> SEQ ID NO 50
<211> LENGTH: 22
<212> TYPE: DNA
<213> ORGANISM: Artificial Sequence

```
<220> FEATURE:
<223> OTHER INFORMATION: Primer

<400> SEQUENCE: 50
attcttgcag ccagctttgc gt                                              22

<210> SEQ ID NO 51
<211> LENGTH: 24
<212> TYPE: DNA
<213> ORGANISM: Artificial Sequence
<220> FEATURE:
<223> OTHER INFORMATION: Primer

<400> SEQUENCE: 51
agctcctcta caggcttgtt cact                                            24

<210> SEQ ID NO 52
<211> LENGTH: 26
<212> TYPE: DNA
<213> ORGANISM: Artificial Sequence
<220> FEATURE:
<223> OTHER INFORMATION: Primer

<400> SEQUENCE: 52
ggacgtgttc aatgctaaca gcaacc                                          26
```